US006660846B1

(12) United States Patent
Edwards et al.

(10) Patent No.: US 6,660,846 B1
(45) Date of Patent: Dec. 9, 2003

(54) VESICULAR AMINO ACID TRANSPORTER COMPOSITION AND METHOD

(75) Inventors: Robert H. Edwards, San Francisco, CA (US); Richard J. Reimer, San Francisco, CA (US); Steven L. McIntire, Tiburon, CA (US); Erik M. Jorgensen, Salt Lake City, UT (US); Kim Schuske, Salt Lake City, UT (US)

(73) Assignees: The Regents of the University of CA, Oakland, CA (US); University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/178,093

(22) Filed: Oct. 23, 1998

Related U.S. Application Data

(60) Provisional application No. 60/063,012, filed on Oct. 23, 1997.

(51) Int. Cl.[7] .................. C07H 21/04; C12N 15/00; C12N 15/63; C07K 14/00
(52) U.S. Cl. .................. 536/23.5; 435/69.1; 435/320.1; 435/325; 435/252.3; 435/70.1; 435/91.2; 435/172.3; 530/300; 530/350
(58) Field of Search .................. 536/23.5; 435/69.1, 435/320.1, 325, 252.3, 70.1, 91.2, 172.3; 530/300, 350

(56) References Cited

U.S. PATENT DOCUMENTS 5,658,786 A 8/1997 Smith et al. .................. 435/365

OTHER PUBLICATIONS

Sagne, c. et al., Cloning of Functional vesicular GABA and glycine transporter by screening of genome databases, vol. 47, pp. 177–183, 1997.*

Alfonso. et al., "The *Caenorhabditis elegans* unc–17 Gene: A Putative Vesicular Acetylcholine Transporter," Science 261:617–619 (1993).
Erickson, J.D., et al., "Expression cloning of a reserpine-–sensitive vesicular monoamine transporter," Proc. Natl. Acad. Sci. USA 89:10993–10997 (1992).
Genbank Accession No. AF030253.
Genbank Accession No. AF031935.
Genbank Accession No. L14269.
Liu, Q–R, et al., "A family of genes encoding neurotransmitter transporters," Proc. Natl. Acad. Sci. USA 89:6639–6643 (1992).
Lin, Y., et al., "cDNA That Suppresses MPP$^+$ Toxicity Encodes a Vesicular Amine Transporter," Cell 70:539–551 (1992).
Liu, Y., et al., "The Role of Vesicular Transport Proteins in Synaptic Transmission and Neural Degeneration," Annu. Rev. Neurosci. 20:125–156 (1997).
McIntire, S.L., et al., "Identification and characterization of the vesicular GABA transporter," Nature 389:870–876 (1997).
Reimer, R.J., "Vesicular neurotransmitter transport and the presynaptic regulation of quantal size," Curr. Opin Neurobiol 8(3):405–412 (1998).

* cited by examiner

*Primary Examiner*—Gary Kunz
*Assistant Examiner*—Nirmal S. Basi
(74) *Attorney, Agent, or Firm*—Perkins Coie LLP; Peter J. Dehlinger; Larry W. Thrower

(57) ABSTRACT

Disclosed are invertebrate and vertebrate synaptic vesicle amino acid transporter compositions which define a novel family of transporter proteins, recombinant vectors and cells comprising nucleic acid sequences encoding vertebrate synaptic vesicle amino acid transporter proteins and antibodies directed against such proteins. Also disclosed are methods for utilizing such compositions in screening assays and treatment regimens.

13 Claims, 11 Drawing Sheets

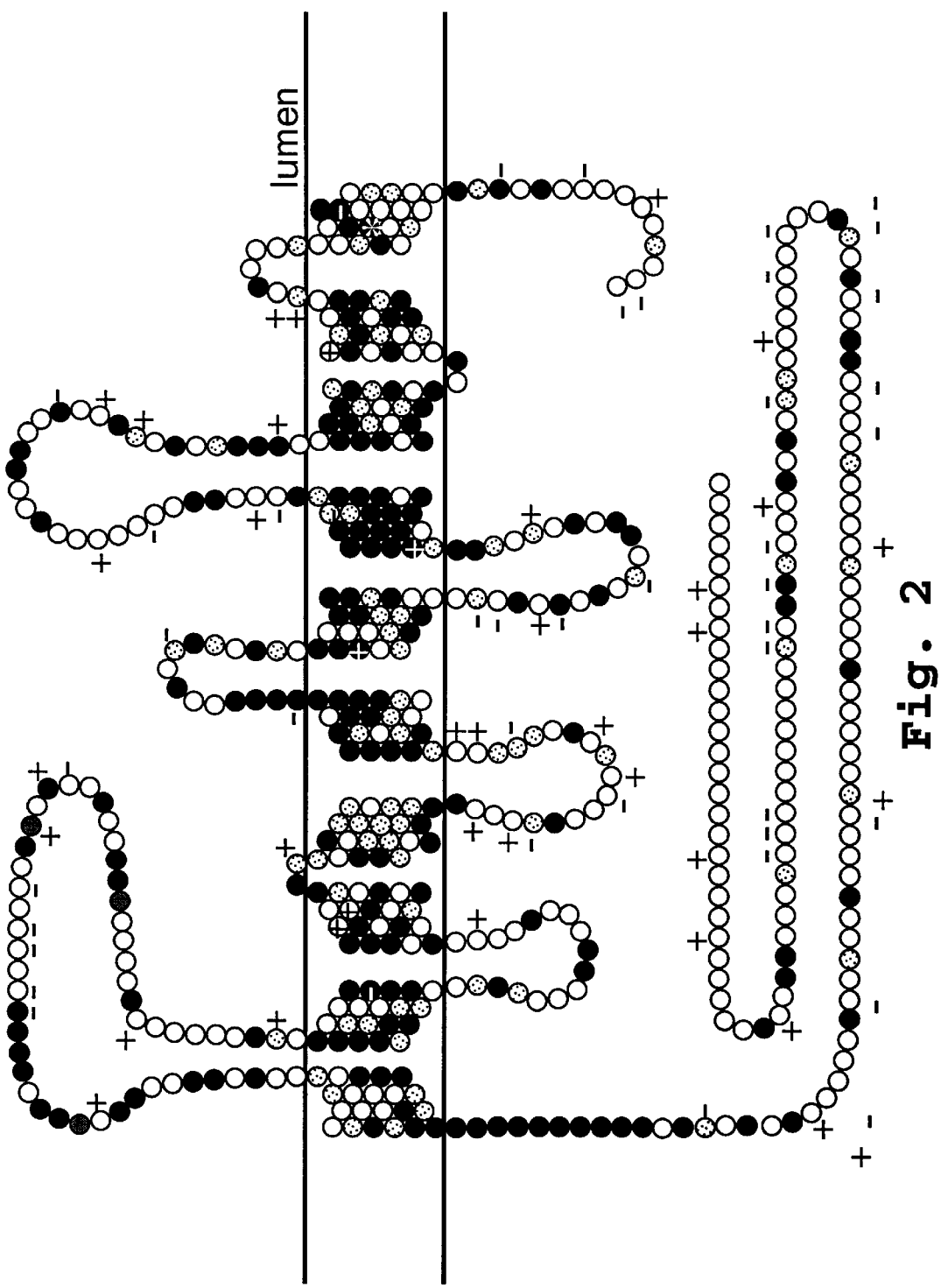

| allele | wild-type sequence | | | mutant sequence | | |
|---|---|---|---|---|---|---|
| e307 | tttccag/GAA | | | tttccaa/GAA | | |
| n2476 | CTT<br>L174 | [ACA....CT]A<br>T175 L221 | CAA<br>Q222 | CTT<br>L174 | [ ] ACA<br>T175 | A<br>N176 |
| n2409 | GGA<br>G(462) | | | AGA<br>R(462) | | |

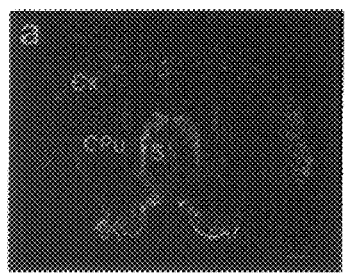 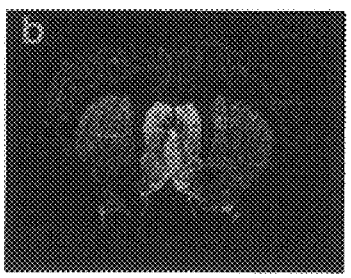 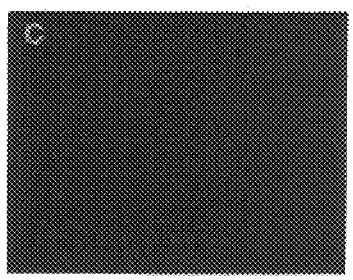
Fig. 8A Fig. 8B Fig. 8C
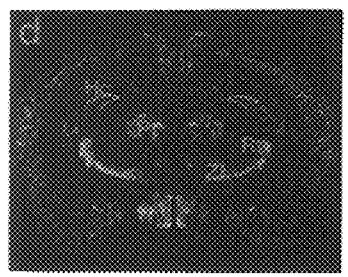  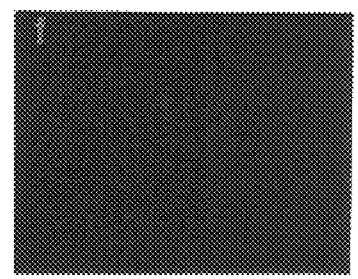
Fig. 8D Fig. 8E Fig. 8F
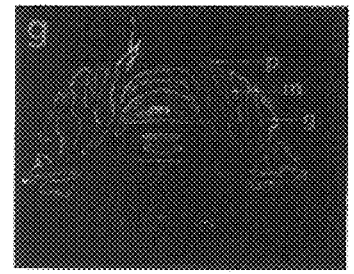 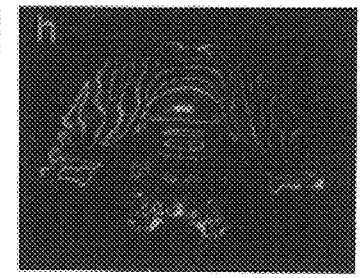 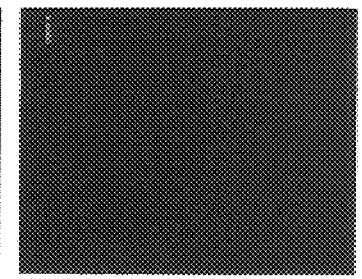
Fig. 8G Fig. 8H Fig. 8I
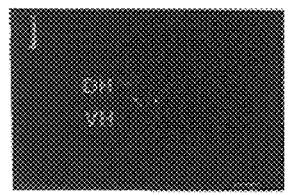 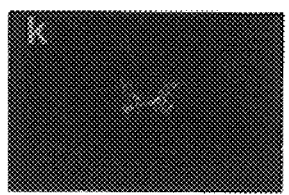 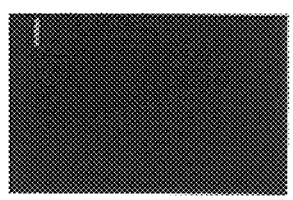
Fig. 8J Fig. 8K Fig. 8L

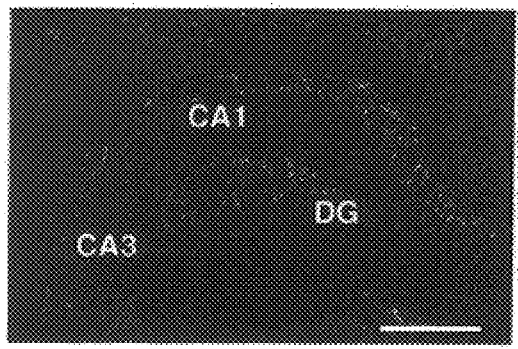 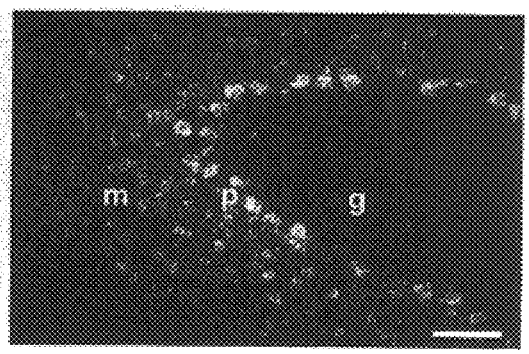
Fig. 9A                    Fig. 9B
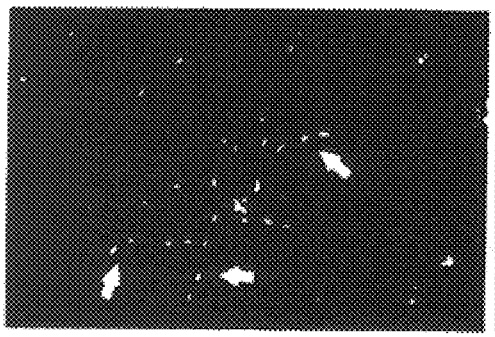 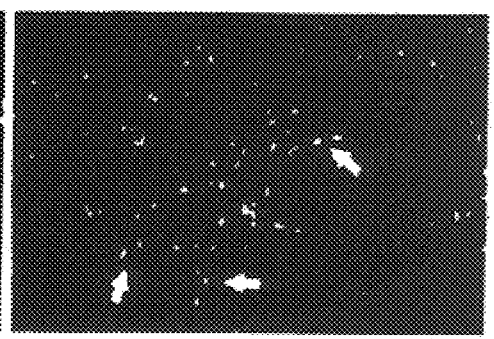
Fig. 10A                   Fig. 10B

SEQUENCE LISTING

<160> NUMBER OF SEQ ID NOS: 50

<210> SEQ ID NO 1
<211> LENGTH: 486
<212> TYPE: PRT
<213> ORGANISM: Caenorhabditis elegans
<220> FEATURE:
<221> NAME/KEY: CHAIN
<222> LOCATION: (1)...(486)
<223> OTHER INFORMATION: UNC-47 polypeptide sequence

<400> SEQUENCE: 1

```
Met Ala Ser Asn Arg Phe Gln Asn Leu Gln Asn Trp Thr Asn Lys His
1               5                   10                  15

Val Phe Ser Asn Ser Leu Asp Tyr Trp Asn Gln Glu Leu Asn Glu Val
            20                  25                  30

Pro Ser Tyr Gln Asn Gln Pro Gln Thr Gly Glu Ser Gly Ser Asn Pro
        35                  40                  45

Pro Pro His Asp Arg Leu Glu Pro Ile Gln Glu Ser Val Val Ser Glu
    50                  55                  60

Gln Pro Gln Lys Asp Asp Ile Asn Lys Gln Glu Ala Lys Asp Asp
65                  70                  75                  80

Gly His Gly Glu Ala Ser Glu Pro Ile Ser Ala Leu Gln Ala Ala Trp
                85                  90                  95

Asn Val Thr Asn Ala Ile Gln Gly Met Phe Ile Val Gly Leu Pro Ile
            100                 105                 110

Ala Val Lys Val Gly Gly Trp Trp Ser Ile Gly Ala Met Val Gly Val
        115                 120                 125

Ala Tyr Val Cys Tyr Trp Thr Gly Val Leu Leu Ile Glu Cys Leu Tyr
    130                 135                 140

Glu Asn Gly Val Lys Lys Arg Lys Thr Tyr Arg Glu Ile Ala Asp Phe
145                 150                 155                 160

Tyr Lys Pro Gly Phe Gly Lys Trp Val Leu Ala Ala Gln Leu Thr Glu
                165                 170                 175

Leu Leu Ser Thr Cys Ile Ile Tyr Leu Val Leu Ala Ala Asp Leu Leu
            180                 185                 190

Gln Ser Cys Phe Pro Ser Val Asp Lys Ala Gly Trp Met Met Ile Thr
        195                 200                 205

Ser Ala Ser Leu Leu Thr Cys Ser Phe Leu Asp Asp Leu Gln Ile Val
    210                 215                 220

Ser Arg Leu Ser Phe Phe Asn Ala Ile Ser His Leu Ile Val Asn Leu
225                 230                 235                 240

Ile Met Val Leu Tyr Cys Leu Ser Phe Val Ser Gln Trp Ser Phe Ser
                245                 250                 255

Thr Ile Thr Phe Ser Leu Asn Ile Asn Thr Leu Pro Thr Ile Val Gly
            260                 265                 270

Met Val Val Phe Gly Tyr Thr Ser His Ile Phe Leu Pro Asn Leu Glu
        275                 280                 285
```

```
Gly Asn Met Lys Asn Pro Ala Gln Phe Asn Val Met Leu Lys Trp Ser
    290                 295                 300

His Ile Ala Ala Ala Val Phe Lys Val Val Phe Gly Met Leu Gly Phe
305                 310                 315                 320

Leu Thr Phe Gly Glu Leu Thr Gln Glu Glu Ile Ser Asn Ser Leu Pro
                325                 330                 335

Asn Gln Ser Phe Lys Ile Leu Val Asn Leu Ile Leu Val Val Lys Ala
                340                 345                 350

Leu Leu Ser Tyr Pro Leu Pro Phe Tyr Ala Ala Val Gln Leu Leu Lys
                355                 360                 365

Asn Asn Leu Phe Leu Gly Tyr Pro Gln Thr Pro Phe Thr Ser Cys Tyr
    370                 375                 380

Ser Pro Asp Lys Ser Leu Arg Glu Trp Ala Val Thr Leu Arg Ile Ile
385                 390                 395                 400

Leu Val Leu Phe Thr Leu Phe Val Ala Leu Ser Val Pro Tyr Leu Val
                405                 410                 415

Glu Leu Met Gly Leu Val Gly Asn Ile Thr Gly Thr Met Leu Ser Phe
                420                 425                 430

Ile Trp Pro Ala Leu Phe His Leu Tyr Ile Lys Glu Lys Thr Leu Asn
                435                 440                 445

Asn Phe Glu Lys Arg Phe Asp Gln Gly Ile Ile Ile Met Gly Cys Ser
    450                 455                 460

Val Cys Ile Ser Gly Val Tyr Phe Ser Ser Met Glu Leu Leu Arg Ala
465                 470                 475                 480

Ile Asn Ser Ala Asp Ser
                485

<210> SEQ ID NO 2
<211> LENGTH: 525
<212> TYPE: PRT
<213> ORGANISM: Rattus norvegicus
<220> FEATURE:
<221> NAME/KEY: CHAIN
<222> LOCATION: (1)...(525)
<223> OTHER INFORMATION: RUNC-47 polypeptide sequence

<400> SEQUENCE: 2

Met Ala Thr Leu Leu Arg Ser Lys Leu Thr Asn Val Ala Thr Ser Val
1               5                   10                  15

Ser Asn Lys Ser Gln Ala Lys Val Ser Gly Met Phe Ala Arg Met Gly
                20                  25                  30

Phe Gln Ala Ala Thr Asp Glu Glu Ala Val Gly Phe Ala His Cys Asp
            35                  40                  45

Asp Leu Asp Phe Glu His Arg Gln Gly Leu Gln Met Asp Ile Leu Lys
        50                  55                  60

Ser Glu Gly Glu Pro Cys Gly Asp Glu Gly Ala Glu Pro Pro Val Glu
65                  70                  75                  80

Gly Asp Ile His Tyr Gln Arg Gly Gly Ala Pro Leu Pro Pro Ser Gly
                85                  90                  95

Ser Lys Asp Gln Ala Val Gly Ala Gly Gly Glu Phe Gly Gly His Asp
                100                 105                 110

Lys Pro Lys Ile Thr Ala Trp Glu Ala Gly Trp Asn Val Thr Asn Ala
            115                 120                 125

Ile Gln Gly Met Phe Val Leu Gly Leu Pro Tyr Ala Ile Leu His Gly
        130                 135                 140
```

```
Gly Tyr Leu Gly Leu Phe Leu Ile Ile Phe Ala Ala Val Val Cys Cys
145                 150                 155                 160

Tyr Thr Gly Lys Ile Leu Ile Ala Cys Leu Tyr Glu Asn Glu Asp
            165                 170                 175

Gly Glu Val Val Arg Val Arg Asp Ser Tyr Val Ala Ile Ala Asn Ala
            180                 185                 190

Cys Cys Ala Pro Arg Phe Pro Thr Leu Gly Gly Arg Val Val Asn Val
        195                 200                 205

Ala Gln Ile Ile Glu Leu Val Met Thr Cys Ile Leu Tyr Val Val Val
    210                 215                 220

Ser Gly Asn Leu Met Tyr Asn Ser Phe Pro Gly Leu Pro Val Ser Gln
225                 230                 235                 240

Lys Ser Trp Ser Ile Ala Thr Ala Val Leu Leu Pro Cys Ala Phe
                245                 250                 255

Leu Lys Asn Leu Lys Ala Val Ser Lys Phe Ser Leu Leu Cys Thr Leu
            260                 265                 270

Ala His Phe Val Ile Asn Ile Leu Val Ile Ala Tyr Cys Leu Ser Arg
        275                 280                 285

Ala Arg Asp Trp Ala Trp Glu Lys Val Lys Phe Tyr Ile Asp Val Lys
    290                 295                 300

Lys Phe Pro Ile Ser Ile Gly Ile Ile Val Phe Ser Tyr Thr Ser Gln
305                 310                 315                 320

Ile Phe Leu Pro Ser Leu Glu Gly Asn Met Gln Gln Pro Ser Glu Phe
                325                 330                 335

His Cys Met Met Asn Trp Thr His Ile Ala Ala Cys Val Leu Lys Gly
            340                 345                 350

Leu Phe Ala Leu Val Ala Tyr Leu Thr Trp Ala Asp Glu Thr Lys Glu
        355                 360                 365

Val Ile Thr Asp Asn Leu Pro Gly Ser Ile Arg Ala Val Val Asn Ile
    370                 375                 380

Phe Leu Val Ala Lys Ala Leu Leu Ser Tyr Pro Leu Pro Phe Phe Ala
385                 390                 395                 400

Ala Val Glu Val Leu Glu Lys Ser Leu Phe Gln Glu Gly Ser Arg Ala
                405                 410                 415

Phe Phe Pro Ala Cys Tyr Gly Gly Asp Gly Arg Leu Lys Ser Trp Gly
            420                 425                 430

Leu Thr Leu Arg Cys Ala Leu Val Val Phe Thr Leu Met Ala Ile
        435                 440                 445

Tyr Val Pro His Phe Ala Leu Leu Met Gly Leu Thr Gly Ser Leu Thr
    450                 455                 460

Gly Ala Gly Leu Cys Phe Leu Leu Pro Ser Leu Phe His Leu Arg Leu
465                 470                 475                 480

Leu Trp Arg Lys Leu Leu Trp His Gln Val Phe Phe Asp Val Ala Ile
                485                 490                 495

Phe Val Ile Gly Gly Ile Cys Ser Val Ser Gly Phe Val His Ser Leu
            500                 505                 510

Glu Gly Leu Ile Glu Ala Tyr Arg Thr Asn Ala Glu Asp
        515                 520                 525

<210> SEQ ID NO 3
<211> LENGTH: 1586
<212> TYPE: DNA
<213> ORGANISM: Caenorhabditis elegans
<220> FEATURE:
<221> NAME/KEY: misc_feature
```

<222> LOCATION: (1)...(1586)
<223> OTHER INFORMATION: UNC-47 cDNA

<400> SEQUENCE: 3

| | | | | | |
|---|---|---|---|---|---|
| atggcgtcga | atagatttca | aaatttgcaa | aattggacaa | ataaacatgt | gttcagcaat | 60 |
| tcgctggact | actggaatca | ggagcttaac | gaggttccat | cctatcagaa | ccaacctcag | 120 |
| acgggagaat | caggatcaaa | tcccccacct | catgaccgct | ggagccaat | tcaagaatca | 180 |
| gttgtttctg | agcaaccaca | aaagacgac | ataaacaaac | aagaagaagc | aaaagacgat | 240 |
| ggacatggaa | aagcatcaga | gccaatatca | gctcttcagg | cagcatggaa | tgtcacaaat | 300 |
| gctatccagg | gaatgtttat | agttggtctt | ccaattgcag | taaaggttgg | tggatggtgg | 360 |
| tctattggtg | caatggttgg | agttgcgtac | gtttgctact | ggacagggt | gctccttatc | 420 |
| gagtgtctat | atgaaaatgg | ggtgaaaaag | cgaaaaacgt | atcgagaaat | tgctgatttc | 480 |
| tacaaacctg | gattcggaaa | atgggttctt | gctgcacaac | ttacagaact | tctatcaact | 540 |
| tgcattatct | atttggtact | tgctgcagac | cttctacaga | gttgttttcc | aagtgttgac | 600 |
| aaagccggat | ggatgatgat | tacctcagca | tctttactaa | cgtgctcatt | tcttgatgat | 660 |
| ctacaaattg | tgtctcgttt | gtcattttc | aatgcaatat | ctcatttgat | tgtcaatctg | 720 |
| atcatggtcc | tttactgtct | gtcattcgtc | tcacaatggt | cttctcaac | gatcacattt | 780 |
| tcattgaata | tcaacactct | tccgacaatt | gttggaatgg | ttgttttcgg | ctacacatct | 840 |
| catatattcc | ttccaaatt | agaaggaaat | atgaaaaatc | ctgctcaatt | caacgtaatg | 900 |
| ttaaaatggt | cacacatcgc | cgctgctgtg | ttcaaagttg | tttttggaat | gctcggattt | 960 |
| ctcacatttg | gagagcttac | acaggaggaa | atttcaaatt | ctctgcctaa | tcaatcattt | 1020 |
| aaaattctgg | tgaacctgat | tttagtggtc | aaggctcttc | tatcatatcc | gttgccattc | 1080 |
| tatgcagctg | ttcaactttt | gaagaacaat | ttgttccttg | gatatcctca | gacaccattc | 1140 |
| acaagttgtt | attcaccgga | taatctttta | cgtgaatggg | ccgttacttt | aagaattatt | 1200 |
| ctagtgcttt | tcacacttt | cgttgcatta | tcagttccat | atttggtaga | gttgatggga | 1260 |
| ttagttggaa | atattacagg | aacaatgtta | tcatttatct | ggccggcact | attccacctt | 1320 |
| tatatcaaag | aaaaaactct | caataatttt | gaaaaacgat | ttgatcaagg | aattataata | 1380 |
| atgggatgta | gtgtgtgcat | ttctggtgtc | tacttctcat | caatggaact | tctcagagca | 1440 |
| atcaactctg | ctgattctta | actcaaaatt | caagacattt | tttaatttgc | cattctgaat | 1500 |
| tagtttaata | tcacagaaca | cttttcctt | gtctttttg | gatgttttaa | taaatataat | 1560 |
| gcttgtgaaa | aaaaaaaaa | aaaaaa | | | | 1586 |

<210> SEQ ID NO 4
<211> LENGTH: 2392
<212> TYPE: DNA
<213> ORGANISM: Rattus norvegicus
<220> FEATURE:
<221> NAME/KEY: misc_feature
<222> LOCATION: (1)...(2392)
<223> OTHER INFORMATION: RUNC-47 cDNA

<400> SEQUENCE: 4

| | | | | | |
|---|---|---|---|---|---|
| agcggagata | gcggcccttg | ctgccttgac | gcgcgcccgc | cgcgtcccca | gacccttctg | 60 |
| tccttttctc | ccgccccgcc | gccgccatgg | ccaccctgct | ccgcagcaag | ctgaccaacg | 120 |
| tggccacctc | tgtgtccaac | aagtcccagg | ccaaggtgag | cggcatgttc | gccaggatgg | 180 |
| ggtttcaggc | ggccacggat | gaggaggcgg | tgggcttcgc | gcactgcgac | gatctcgact | 240 |

-continued

| | |
|---|---|
| ttgagcaccg ccagggcctg cagatggaca tcctgaaatc ggaaggcgag ccctgcgggg | 300 |
| acgagggcgc agaacctccc gtcgagggag acattcatta tcagcgcggc ggcgctcccc | 360 |
| tgccaccctc gggctccaag gaccaggccg tgggagctgg tggggagttc gggggtcacg | 420 |
| acaaacccaa gatcacggcg tgggaagcgg gctggaacgt gacaaacgcc attcagggca | 480 |
| tgttcgtgct gggtctaccc tacgccatcc tccacggcgg ctacctgggg ttgttcctca | 540 |
| tcatcttcgc cgcggtggtg tgctgctaca ccggcaagat cctcatcgcg tgcctgtacg | 600 |
| aggagaacga agatggtgag gtggtgcgcg tgagggactc gtatgtggcc atagctaacg | 660 |
| cgtgctgcgc tcctcgattc cccacgctgg gcggccgcgt ggtcaatgtg cccagatca | 720 |
| tcgagctggt gatgacgtgt atcttgtacg tagtggtgag cggcaacctc atgtacaaca | 780 |
| gtttcccggg gctgcccgtg tcgcagaagt cctggtccat catagccacg gcggtgctgc | 840 |
| tgccctgcgc cttcctgaag aatctcaagg ccgtgtccaa gttcagtctg ctgtgcacgc | 900 |
| tggcccactt cgtcatcaac atcctggtca tcgcctactg tctctcgcgc gcgcgtgact | 960 |
| gggcctggga gaaggtgaag ttctacatcg acgtcaagaa gtttcctatc tccatcggca | 1020 |
| tcatcgtgtt cagctacacg tcgcagatct tcctgccctc gctcgaaggc aacatgcagc | 1080 |
| agcccagcga attccactgc atgatgaact ggacacacat cgccgcctgc gtgctcaagg | 1140 |
| gtctcttcgc gctcgtcgcc tacctcacct gggccgacga gaccaaggaa gtcatcacgg | 1200 |
| ataacctgcc cggttccatc cgcgccgtgg tcaacatctt cctggtggcc aaggcgctgc | 1260 |
| tgtcctaccc gttgcccttc ttcgcggccg tcgaagtgct ggagaagtct ctcttccagg | 1320 |
| aaggcagtcg tgccttcttc cccgcctgct acggtggcga cggtcgcctt aagtcctggg | 1380 |
| ggctgacgct gcgctgcgcg ctggtggtct tcacgctgct catggccatc tacgtgccac | 1440 |
| acttcgcgct gctcatgggc ctcacgggca gcctcacggg agccggcctc tgcttcctgc | 1500 |
| tgcccagcct cttccacttg cgtcttctct ggcgcaagct gctgtggcac caggtcttct | 1560 |
| tcgatgtggc catcttcgtc atcggcggca tctgcagcgt gtccggcttc gtgcattcac | 1620 |
| tcgagggcct catcgaggcc taccgaacca acgcagagga ctaggggggcg ggaccctgc | 1680 |
| ccccagctcc ctccccgccc accccactc cccttatcc ccgcccccaa ccccaccccc | 1740 |
| cagcccctg cgcaaccacg ctgggagagc cgagctttaa acacctccgg ttcctagttg | 1800 |
| ctgattattc ggggaccggg cgggggaggg aggggggatag acatccaagg tccactgcgt | 1860 |
| ctgcgtttct gtcgttcttt ctattccaca tcgtcctgat ttgggggggag ggagcagagc | 1920 |
| gtataagtga agggtatttt ctgtccttcc tagaacaccc accaccacca ccaccaaact | 1980 |
| ttggctccag tcaatgttag gggtgggaag ggaggggggaa agggaacacg cagttcgcag | 2040 |
| gctcggaaac ttgaccttgg gggtggggtg ggggacattt cacagccatt cagtgcttgg | 2100 |
| aatctactgc gtccagccat ttccagcaag agcgctcccc atgccctaga catttcaacc | 2160 |
| ttgaggcctg aaaggctgac cgggaaatcc atttcgggca ggcgacttcc ctctggagaa | 2220 |
| gccgcggcag gggccccgt ttgcctgccg gttttcagga acccaaactc atcttgtgca | 2280 |
| atgtatccgg ttgtggaact gtatactgtg cgtgtggtgt gctcgtggtg aataagatga | 2340 |
| aatgtatatc agaaaaaatc tatctctaat ttagagtgcg gtgcctcgtg cc | 2392 |

<210> SEQ ID NO 5
<211> LENGTH: 21
<212> TYPE: PRT
<213> ORGANISM: Rattus norvegicus

<400> SEQUENCE: 5

-continued

Phe Val Leu Gly Leu Pro Tyr Ala Ile Leu His Gly Gly Tyr Leu Gly
 1               5                   10                  15

Leu Phe Leu Ile Ile
             20

<210> SEQ ID NO 6
<211> LENGTH: 20
<212> TYPE: PRT
<213> ORGANISM: Rattus norvegicus

<400> SEQUENCE: 6

Val Asn Val Ala Gln Ile Ile Glu Leu Val Met Thr Cys Ile Leu Tyr
 1               5                   10                  15

Val Val Val Ser
             20

<210> SEQ ID NO 7
<211> LENGTH: 21
<212> TYPE: PRT
<213> ORGANISM: Rattus norvegicus

<400> SEQUENCE: 7

Trp Ser Ile Ile Ala Thr Ala Val Leu Leu Pro Cys Ala Phe Leu Lys
 1               5                   10                  15

Asn Leu Lys Ala Val
             20

<210> SEQ ID NO 8
<211> LENGTH: 21
<212> TYPE: PRT
<213> ORGANISM: Rattus norvegicus

<400> SEQUENCE: 8

Phe Ser Leu Leu Cys Thr Leu Ala His Phe Val Ile Asn Ile Leu Val
 1               5                   10                  15

Ile Ala Tyr Cys Leu
             20

<210> SEQ ID NO 9
<211> LENGTH: 21
<212> TYPE: PRT
<213> ORGANISM: Rattus norvegicus

<400> SEQUENCE: 9

Phe Pro Ile Ser Ile Gly Ile Ile Val Phe Ser Tyr Thr Ser Gln Ile
 1               5                   10                  15

Phe Leu Pro Ser Leu
             20

<210> SEQ ID NO 10
<211> LENGTH: 21
<212> TYPE: PRT
<213> ORGANISM: Rattus norvegicus

<400> SEQUENCE: 10

Trp Thr His Ile Ala Ala Cys Val Leu Lys Gly Leu Phe Ala Leu Val
 1               5                   10                  15

Ala Tyr Leu Thr Trp
             20

<210> SEQ ID NO 11

```
<211> LENGTH: 19
<212> TYPE: PRT
<213> ORGANISM: Rattus norvegicus

<400> SEQUENCE: 11

Ile Phe Leu Val Ala Lys Ala Leu Leu Ser Tyr Pro Leu Pro Phe Phe
 1               5                  10                  15

Ala Ala Val

<210> SEQ ID NO 12
<211> LENGTH: 22
<212> TYPE: PRT
<213> ORGANISM: Rattus norvegicus

<400> SEQUENCE: 12

Ala Leu Val Val Phe Thr Leu Leu Met Ala Ile Tyr Val Pro His Phe
 1               5                  10                  15

Ala Leu Leu Met Gly Leu
             20

<210> SEQ ID NO 13
<211> LENGTH: 21
<212> TYPE: PRT
<213> ORGANISM: Rattus norvegicus

<400> SEQUENCE: 13

Ser Leu Thr Gly Ala Gly Leu Cys Phe Leu Leu Pro Ser Leu Phe His
 1               5                  10                  15

Leu Arg Leu Leu Trp
             20

<210> SEQ ID NO 14
<211> LENGTH: 20
<212> TYPE: PRT
<213> ORGANISM: Rattus norvegicus

<400> SEQUENCE: 14

Val Phe Phe Asp Val Ala Ile Phe Val Ile Gly Ile Cys Ser Val
 1               5                  10                  15

Ser Gly Phe Val
             20

<210> SEQ ID NO 15
<211> LENGTH: 21
<212> TYPE: PRT
<213> ORGANISM: Caenorhabditis elegans

<400> SEQUENCE: 15

Phe Ile Val Gly Leu Pro Ile Ala Val Lys Val Gly Gly Trp Trp Ser
 1               5                  10                  15

Ile Gly Ala Met Val
             20

<210> SEQ ID NO 16
<211> LENGTH: 20
<212> TYPE: PRT
<213> ORGANISM: Caenorhabditis elegans

<400> SEQUENCE: 16

Val Leu Ala Ala Gln Leu Thr Glu Leu Leu Ser Thr Cys Ile Ile Tyr
 1               5                  10                  15

Leu Val Leu Ala
```

```
<210> SEQ ID NO 17
<211> LENGTH: 21
<212> TYPE: PRT
<213> ORGANISM: Caenorhabditis elegans

<400> SEQUENCE: 17

Trp Met Met Ile Thr Ser Ala Ser Leu Leu Thr Cys Ser Phe Leu Asp
 1               5                  10                  15

Asp Leu Gln Ile Val
            20

<210> SEQ ID NO 18
<211> LENGTH: 21
<212> TYPE: PRT
<213> ORGANISM: Caenorhabditis elegans

<400> SEQUENCE: 18

Leu Ser Phe Phe Asn Ala Ile Ser His Leu Ile Val Asn Leu Ile Met
 1               5                  10                  15

Val Leu Tyr Cys Leu
            20

<210> SEQ ID NO 19
<211> LENGTH: 21
<212> TYPE: PRT
<213> ORGANISM: Caenorhabditis elegans

<400> SEQUENCE: 19

Leu Pro Thr Ile Val Gly Met Val Val Phe Gly Tyr Thr Ser His Ile
 1               5                  10                  15

Phe Leu Pro Asn Leu
            20

<210> SEQ ID NO 20
<211> LENGTH: 21
<212> TYPE: PRT
<213> ORGANISM: Caenorhabditis elegans

<400> SEQUENCE: 20

Trp Ser His Ile Ala Ala Ala Val Phe Lys Val Val Phe Gly Met Leu
 1               5                  10                  15

Gly Phe Leu Thr Phe
            20

<210> SEQ ID NO 21
<211> LENGTH: 19
<212> TYPE: PRT
<213> ORGANISM: Caenorhabditis elegans

<400> SEQUENCE: 21

Leu Ile Leu Val Val Lys Ala Leu Leu Ser Tyr Pro Leu Pro Phe Tyr
 1               5                  10                  15

Ala Ala Val

<210> SEQ ID NO 22
<211> LENGTH: 22
<212> TYPE: PRT
<213> ORGANISM: Caenorhabditis elegans

<400> SEQUENCE: 22
```

Ile Leu Val Leu Phe Thr Leu Phe Val Ala Leu Ser Val Pro Tyr Leu
1               5                   10                  15

Val Glu Leu Met Gly Leu
            20

<210> SEQ ID NO 23
<211> LENGTH: 21
<212> TYPE: PRT
<213> ORGANISM: Caenorhabditis elegans

<400> SEQUENCE: 23

Asn Ile Thr Gly Thr Met Leu Ser Phe Ile Trp Pro Ala Leu Phe His
1               5                   10                  15

Leu Tyr Ile Lys Glu
            20

<210> SEQ ID NO 24
<211> LENGTH: 21
<212> TYPE: PRT
<213> ORGANISM: Caenorhabditis elegans

<400> SEQUENCE: 24

Lys Arg Phe Asp Gln Gly Ile Ile Ile Met Gly Cys Ser Val Cys Ile
1               5                   10                  15

Ser Gly Val Tyr Phe
            20

<210> SEQ ID NO 25
<211> LENGTH: 2363
<212> TYPE: DNA
<213> ORGANISM: Artificial Sequence
<220> FEATURE:
<223> OTHER INFORMATION: synthetic nucleotide (RVT2 nucleotide sequence)
<221> NAME/KEY: misc_feature
<222> LOCATION: (2036)...(2036)
<223> OTHER INFORMATION: n = A,T,C or G

<400> SEQUENCE: 25
gagcggccgc cagtgtgctc taaaggacct ggagacccc gagggatgga agcgccggcg      60 ccggcgagg cggcgggatg cgaggagctc gatatggacg tgatgaggcc cttaataaac      120
gaacagaatt tcgatgggtc gtccgacgag gagcaggaac agacgcttct gcccatgcag     180
aaacactacc agctcgatgg gcagcatggg atttcgtttg tgcagacctt gatgcacctt     240
ctcaagggga acattggaac cggcctctta gggcttccct tggcaataaa gaatgcaggc     300
atcgtgcttg gaccaatcag ccttgtgttt ataggaatta tttccgtcca ctgtatgcac     360
atattggtac gttgcagtca ctttctatgt cagaggttta agaagtcaac gttggggtac     420
agtgacactg tgagtttttgc catggaggcc agcccgtgga gttgtcttca gaggcaggca     480
gcgtgggggc ggagcgtggt cgacttcttt ctggtgataa cacagctggg attctgcagt     540
gtctatattg tcttcttagc tgagaatgtg aaacaggttc atgaaggact cctggagacc     600
acagtggtcg tttcgaatag ctcggatctg tctcaagtct gtgagaggag aagtgtggac     660
ctcagggtct acatgctctg ctttctccca cttctaattc tcttggtgtt cattcgagag     720
ctgaagagtc tctttgtact ctcattcctt gccaacattt ccatggctgc cagtctcgtg     780
ataatttacc agtatgttgt taggagcatg ccggatcccc acaaccttcc gatagtcgcg     840
gggtggaaga ataccccact gttcttcggt accgctgtgt ttgctttttga aggcataggc     900 gtggtgctgc cactggaaaa ccaaatgaga gagtccaagc gcttccctca ggcgttgaac     960

-continued

```
attggcatgg ccatcgtcac ggtgctgtac atcagcctgg ccacgttagg ctacatgtgt      1020
ttccgagatg agatcaaagg cagcataaca ctgaatcttc cccaggacat gtggttgtat      1080
cagtcagtga aaatcctgta ttcctttggc atttttgtga cctattctat tcagttctat      1140
gtcccagcag agatcattat ccccgcagtc actgctagac ttcatgccaa atggaagtgc      1200
atctgtgact tgggatacg gtccctcttg gttagtatca cctgtgctgg cgcggttctc       1260
attccccgcc tggacattgt gatctccttc gtggggctg tgagtagcag cactctagcc       1320
ctgatcctgc ccccgcttgt ggagatcctg acgttttcca aggaccatta caacgtatgg      1380
atggtcctga agaacatttc catagcgttc actgggttcg tgggcttctt gttgggcacg      1440
tatgtcaccg tcgaagaaat tatttatcca actacagcag ttgctgatgg cgcctcccag      1500
agtctctctc tgaacgtgaa ctctacatgt gtatcaagtg gtttgtaata gtgggagaag      1560
agcggtgaac cctccgttgt cacccccagtt ctaacagcaa tcaagaacgg gtacagtgta    1620
tcgccataca ctaaacacag tgccaaactc ctgtttttgt tggcagagta ttgtaatttg     1680
actgtgaact gacatctttt gtagctgtga taaactatag cagattattg cttttatcta    1740
atgacaatga aacattttaa attagctttg aagactgaaa aagtttaaaa ttcaaaacgg     1800
aaacaataag catagcctgt tattctttgt ttctgtaaga aatactttgg gtcatctttc    1860
ttaccaccat tgagaagaca aaggatttca acatggtata aattaaatag gggcatagtt    1920
ttaaaaacct cttggaagca tcccacaata gcagtgttta cctcctgtgt acgtgtgcac    1980
aaaaatgcac tgatggtgtt ttcttccgtg ggtgatgctg ctgacggggc gatgcnttgg    2040
agggatggca gattcccact gaccaccgtg tgagcagtag agcgttccca gagccagagt    2100
cgctttattg tgcagctatt cagagggtag agcgtcacgg tcactgagca aggctctgac    2160
ttcctgtttc agtcgtaggt gaaaaggtca cggaggtatc tggaatatcg ctcccttagt    2220
tctgtcttaa cttaagggag ttattgctcc cttagttgtt ctgtcttaac ttagggagt     2280 tattgctctc tcagttgggt ttctgtcact gatacaacag cacaaccaga agcaattctg    2340
caggagaagg cttcagttta cag                                             2363
```

<210> SEQ ID NO 26
<211> LENGTH: 500
<212> TYPE: PRT
<213> ORGANISM: Artificial Sequence
<220> FEATURE:
<223> OTHER INFORMATION: synthetic peptide (RVT2 polypeptide sequence)

<400> SEQUENCE: 26

```
Met Glu Ala Pro Ala Pro Ala Glu Ala Ala Gly Cys Glu Glu Leu Asp
  1               5                  10                  15

Met Asp Val Met Arg Pro Leu Ile Asn Glu Gln Asn Phe Asp Gly Ser
                 20                  25                  30

Ser Asp Glu Glu Gln Glu Gln Thr Leu Leu Pro Met Gln Lys His Tyr
             35                  40                  45

Gln Leu Asp Gly Gln His Gly Ile Ser Phe Val Gln Thr Leu Met His
         50                  55                  60

Leu Leu Lys Gly Asn Ile Gly Thr Gly Leu Leu Gly Leu Pro Leu Ala
 65                  70                  75                  80

Ile Lys Asn Ala Gly Ile Val Leu Gly Pro Ile Ser Leu Val Phe Ile
                 85                  90                  95

Gly Ile Ile Ser Val His Cys Met His Ile Leu Val Arg Cys Ser His
            100                 105                 110
```

```
Phe Leu Cys Gln Arg Phe Lys Lys Ser Thr Leu Gly Tyr Ser Asp Thr
        115                 120                 125

Val Ser Phe Ala Met Glu Ala Ser Pro Trp Ser Cys Leu Gln Arg Gln
    130                 135                 140

Ala Ala Trp Gly Arg Ser Val Val Asp Phe Leu Val Ile Thr Gln
145                 150                 155                 160

Leu Gly Phe Cys Ser Val Tyr Ile Val Phe Leu Ala Glu Asn Val Lys
                165                 170                 175

Gln Val His Glu Gly Leu Leu Glu Thr Thr Val Val Ser Asn Ser
            180                 185                 190

Ser Asp Leu Ser Gln Val Cys Glu Arg Arg Ser Val Asp Leu Arg Val
        195                 200                 205

Tyr Met Leu Cys Phe Leu Pro Leu Leu Ile Leu Leu Val Phe Ile Arg
    210                 215                 220

Glu Leu Lys Ser Leu Phe Val Leu Ser Phe Leu Ala Asn Ile Ser Met
225                 230                 235                 240

Ala Ala Ser Leu Val Ile Ile Tyr Gln Tyr Val Val Arg Ser Met Pro
                245                 250                 255

Asp Pro His Asn Leu Pro Ile Val Ala Gly Trp Lys Lys Tyr Pro Leu
            260                 265                 270

Phe Phe Gly Thr Ala Val Phe Ala Phe Glu Gly Ile Gly Val Val Leu
        275                 280                 285

Pro Leu Glu Asn Gln Met Arg Glu Ser Lys Arg Phe Pro Gln Ala Leu
    290                 295                 300

Asn Ile Gly Met Ala Ile Val Thr Val Leu Tyr Ile Ser Leu Ala Thr
305                 310                 315                 320

Leu Gly Tyr Met Cys Phe Arg Asp Glu Ile Lys Gly Ser Ile Thr Leu
                325                 330                 335

Asn Leu Pro Gln Asp Met Trp Leu Tyr Gln Ser Val Lys Ile Leu Tyr
            340                 345                 350

Ser Phe Gly Ile Phe Val Thr Tyr Ser Ile Gln Phe Tyr Val Pro Ala
        355                 360                 365

Glu Ile Ile Ile Pro Ala Val Thr Ala Arg Leu His Ala Lys Trp Lys
    370                 375                 380

Cys Ile Cys Asp Phe Gly Ile Arg Ser Leu Leu Val Ser Ile Thr Cys
385                 390                 395                 400

Ala Gly Ala Val Leu Ile Pro Arg Leu Asp Ile Val Ile Ser Phe Val
                405                 410                 415

Gly Ala Val Ser Ser Thr Leu Ala Leu Ile Leu Pro Pro Leu Val
            420                 425                 430

Glu Ile Leu Thr Phe Ser Lys Asp His Tyr Asn Val Trp Met Val Leu
        435                 440                 445

Lys Asn Ile Ser Ile Ala Phe Thr Gly Phe Val Gly Phe Leu Leu Gly
    450                 455                 460

Thr Tyr Val Thr Val Glu Glu Ile Ile Tyr Pro Thr Thr Ala Val Ala
465                 470                 475                 480

Asp Gly Ala Ser Gln Ser Leu Ser Leu Asn Val Asn Ser Thr Cys Val
                485                 490                 495

Ser Ser Gly Leu
            500

<210> SEQ ID NO 27
<211> LENGTH: 2392
<212> TYPE: DNA
```

<213> ORGANISM: Artificial Sequence
<220> FEATURE:
<223> OTHER INFORMATION: synthetic nucleotide (RVT3 nucleotide sequence)

<400> SEQUENCE: 27

```
gtggatcccc cgggctgcag gaattcggca cgagctggaa cggagtgctg aacgtgccca      60
ccacgaggcc agatacctga cggtgtttgt gtgagagcgg tgctctgggg tggtttcaga     120
gccatggaga taccccgaca gacagagatg gtggagctgg tgcccaatgg caaacacctg     180
gaggggcttc taccagtggg catgcccacg gcagacaccc agagggctga agacgcccaa     240
cactgtggag agggcaaggg cttccttcag caaagctcca gcaaggagcc acacttcacc     300
gatttcgagg ggaagacatc gtttgggatg tcggtgttca atctcagcaa cgccatcatg     360
ggcagtggca tcctggggct cgcctatgcc atggccaata cgggcatcat cctcttcctg     420
ttcctgctta cggcggttgc cctgttgtct agctactcca ttcacctgct cctcaagtct     480
tctgggattg tgggcatccg tgcctatgag cagttgggct accgtgcctt gggaccccca     540
ggaaagctgg cagcagcctt ggccatcacg cttcagaaca ttggagccat gtccagctat     600
ctgtacatca tcaagtctga actgcctctt gtcatacaga ccttcctgaa tctggagaag     660
ccaaccccgg tgtggtacat ggatggcaac taccttgtga tcctggtatc cgtcatcatc     720
attctgcccc tggcactaat gcgacagctt ggctacctgg gctactccag tggcttctct     780
ctcagctgca tggtgttctt cttgatcgca gtcatctaca agaagttcca agtgccttgc     840
ccactggcac acaacttggt caatgccaca ggtaacttca gccacatggt ggtggtggag     900
gagaagtcgc agctgcagag cgaacctgac actgctgaag ccttctgcac cccaagctac     960
ttcacactca actcacagac ggcatacacc atccccatca tggccttcgc ctttgtctgc    1020
caccctgagg tgctgcccat atatacggag ctcaaggacc cctccaagag gaagatgcag    1080
cacatctcca acctgtccat tgctgtcatg tatgtcatgt acttcctggc tgccctcttc    1140
ggctacctca ccttctatga cggggtggag tcagagctgc tgcacaccta cagcaaggtg    1200
gacccatttg atgtgctgat cttgtgtgtg cgcgtggccg tgctgatagc ggtcacactt    1260
acggttccga tcgttctgtt cccggtacga cgggccatcc agcagatgct gtttcagaac    1320
caggagttca gctggttgcg gcacgtgctt attgccaccg gcctccttac ttgcatcaac    1380
ttgctggtta tcttcgcccc caacatcttg gcatatttg ggatcattgg tgctacatct    1440
gctccgtgcc tcatcttcat cttccctgcc atcttctact tccgaatcat gcccactgag    1500
aaggagcctg tgagatccac ccccaaaatc ctggcccttt gctttgctgc ggttggcttc    1560
ttgctgatga ccatgagttt gagtttcatc atcactgact gggtctctgg gaccagccaa    1620
catggaggaa accattagga tgacctccat cttgctctgt ttattcctcc tagtaccccc    1680
tgccctctct ctctccagcc cctgctccca gccaggggcc aaggaagggg agaaagacag    1740
gggagaaaga ctctgtaaat actatggcat ttggctccac ccatatcctc tccgtcggaa    1800
ggttttttgtt gaagagccaa ggcccttgga ccacccctgc tgggctccag agctgcaggg    1860
gcttcctgca ctaggaacag ggtggggctg tcgccttaga tcccaccgaa accctccatc    1920
ctcctccagc agctgtgtac actgaggcct agcagccacc tcctgaggtc acacaggctg    1980
cagggcaca cagagccaga acccaggtct gaagacatcc cctagtcctg ctgggagccc    2040
acagtccctg gtctccagct ccttttccaa cacttggggc cccaagtctt agatacaggg    2100
gcccttcctc ttccatctcg tccgtatgaa aacacttgtc ccaacccata tctggggtca    2160
gcagtttctg ctgaagatgg ggctggtgtg taccccagaa atccctgct gttggacctt    2220
```

```
caccactcct ggggaggctg ggactcccac atcctcaagc ccgagctatg acttacattc    2280
cactgctggg agaagagagg cggggcccag agtatcctgc ccttgggagt caaagaccct    2340
aggagccagg ctggcacagg ggatgggag gcctcgtgcc gaattcgata tc             2392
```

<210> SEQ ID NO 28
<211> LENGTH: 504
<212> TYPE: PRT
<213> ORGANISM: Artificial Sequence
<220> FEATURE:
<223> OTHER INFORMATION: synthetic peptide (RVT3 polypeptide sequence)

<400> SEQUENCE: 28

```
Met Glu Ile Pro Arg Gln Thr Glu Met Val Glu Leu Val Pro Asn Gly
 1               5                  10                  15

Lys His Leu Glu Gly Leu Leu Pro Val Gly Met Pro Thr Ala Asp Thr
                20                  25                  30

Gln Arg Ala Glu Asp Ala Gln His Cys Gly Glu Gly Lys Gly Phe Leu
            35                  40                  45

Gln Gln Ser Ser Ser Lys Glu Pro His Phe Thr Asp Phe Glu Gly Lys
        50                  55                  60

Thr Ser Phe Gly Met Ser Val Phe Asn Leu Ser Asn Ala Ile Met Gly
65                  70                  75                  80

Ser Gly Ile Leu Gly Leu Ala Tyr Ala Met Ala Asn Thr Gly Ile Ile
                85                  90                  95

Leu Phe Leu Phe Leu Leu Thr Ala Val Ala Leu Leu Ser Ser Tyr Ser
            100                 105                 110

Ile His Leu Leu Leu Lys Ser Ser Gly Ile Val Gly Ile Arg Ala Tyr
        115                 120                 125

Glu Gln Leu Gly Tyr Arg Ala Phe Gly Thr Pro Gly Lys Leu Ala Ala
    130                 135                 140

Ala Leu Ala Ile Thr Leu Gln Asn Ile Gly Ala Met Ser Ser Tyr Leu
145                 150                 155                 160

Tyr Ile Ile Lys Ser Glu Leu Pro Leu Val Ile Gln Thr Phe Leu Asn
                165                 170                 175

Leu Glu Lys Pro Thr Pro Val Trp Tyr Met Asp Gly Asn Tyr Leu Val
            180                 185                 190

Ile Leu Val Ser Val Ile Ile Leu Pro Leu Ala Leu Met Arg Gln
        195                 200                 205

Leu Gly Tyr Leu Gly Tyr Ser Ser Gly Phe Ser Leu Ser Cys Met Val
    210                 215                 220

Phe Phe Leu Ile Ala Val Ile Tyr Lys Lys Phe Gln Val Pro Cys Pro
225                 230                 235                 240

Leu Ala His Asn Leu Val Asn Ala Thr Gly Asn Phe Ser His Met Val
                245                 250                 255

Val Val Glu Glu Lys Ser Gln Leu Gln Ser Glu Pro Asp Thr Ala Glu
            260                 265                 270

Ala Phe Cys Thr Pro Ser Tyr Phe Thr Leu Asn Ser Gln Thr Ala Tyr
        275                 280                 285

Thr Ile Pro Ile Met Ala Phe Ala Phe Val Cys His Pro Glu Val Leu
    290                 295                 300

Pro Ile Tyr Thr Glu Leu Lys Asp Pro Ser Lys Arg Lys Met Gln His
305                 310                 315                 320

Ile Ser Asn Leu Ser Ile Ala Val Met Tyr Val Met Tyr Phe Leu Ala
                325                 330                 335
```

```
Ala Leu Phe Gly Tyr Leu Thr Phe Tyr Asp Gly Val Glu Ser Glu Leu
                340                 345                 350

Leu His Thr Tyr Ser Lys Val Asp Pro Phe Asp Val Leu Ile Leu Cys
            355                 360                 365

Val Arg Val Ala Val Leu Ile Ala Val Thr Leu Thr Val Pro Ile Val
        370                 375                 380

Leu Phe Pro Val Arg Arg Ala Ile Gln Gln Met Leu Phe Gln Asn Gln
385                 390                 395                 400

Glu Phe Ser Trp Leu Arg His Val Leu Ile Ala Thr Gly Leu Leu Thr
                405                 410                 415

Cys Ile Asn Leu Leu Val Ile Phe Ala Pro Asn Ile Leu Gly Ile Phe
            420                 425                 430

Gly Ile Ile Gly Ala Thr Ser Ala Pro Cys Leu Ile Phe Ile Phe Pro
        435                 440                 445

Ala Ile Phe Tyr Phe Arg Ile Met Pro Thr Glu Lys Glu Pro Val Arg
    450                 455                 460

Ser Thr Pro Lys Ile Leu Ala Leu Cys Phe Ala Ala Val Gly Phe Leu
465                 470                 475                 480

Leu Met Thr Met Ser Leu Ser Phe Ile Ile Thr Asp Trp Val Ser Gly
                485                 490                 495

Thr Ser Gln His Gly Gly Asn His
            500
```

<210> SEQ ID NO 29
<211> LENGTH: 10
<212> TYPE: DNA
<213> ORGANISM: Artificial Sequence
<220> FEATURE:
<223> OTHER INFORMATION: wild-type UNC-47 sequence

<400> SEQUENCE: 29
tttccaggaa                                                          10

<210> SEQ ID NO 30
<211> LENGTH: 12
<212> TYPE: DNA
<213> ORGANISM: Artificial Sequence
<220> FEATURE:
<223> OTHER INFORMATION: wild-type UNC-47 sequence

<400> SEQUENCE: 30
cttacactac aa                                                       12

<210> SEQ ID NO 31
<211> LENGTH: 10
<212> TYPE: DNA
<213> ORGANISM: Artificial Sequence
<220> FEATURE:
<223> OTHER INFORMATION: mutant UNC-47 sequence

<400> SEQUENCE: 31
tttccaagaa                                                          10

<210> SEQ ID NO 32
<211> LENGTH: 7
<212> TYPE: DNA
<213> ORGANISM: Artificial Sequence
<220> FEATURE:
<223> OTHER INFORMATION: mutant UNC-47 sequence

<400> SEQUENCE: 32 cttacaa                                                                7

<210> SEQ ID NO 33
<211> LENGTH: 36
<212> TYPE: PRT
<213> ORGANISM: Caenorhabditis elegans

<400> SEQUENCE: 33

Lys His Lys Ile Gly Trp Val Ile Ala Ala Ile Phe Ile Ile Ala Asp
1               5                   10                  15

Met Val Gly Gly Gly Val Val Ala Met Pro Val Ala Phe Lys Leu Ser
            20                  25                  30

Gly Leu Pro Met
        35

<210> SEQ ID NO 34
<211> LENGTH: 86
<212> TYPE: PRT
<213> ORGANISM: Caenorhabditis elegans

<400> SEQUENCE: 34

Thr Ser Thr Ser Thr Ile Leu Ser Phe Gly Ile Phe Leu Phe Ala Phe
1               5                   10                  15

Ser Gly His Tyr Val Phe Pro Thr Ile Gln His Asp Met Lys Asn Pro
            20                  25                  30

Arg Asp Phe Thr Lys Ser Ile Phe Ala Gly Phe Leu Gly Val Val Ile
        35                  40                  45

Leu Tyr Leu Pro Leu Cys Ile Phe Ala Phe Val Val Tyr Gly Asp Ser
    50                  55                  60

Met Thr Asp Ser Val Ile Tyr Ser Ile Gln Ser Pro Ser Leu Gln Leu
65                  70                  75                  80

Leu Ala Asn Leu Met Ile
                85

<210> SEQ ID NO 35
<211> LENGTH: 49
<212> TYPE: PRT
<213> ORGANISM: Caenorhabditis elegans

<400> SEQUENCE: 35

Arg Val Ile Thr Arg Thr Ile Val Leu Phe Leu Val Leu Phe Val Ala
1               5                   10                  15

Leu Thr Val Pro Asp Phe Gln Pro Val Met Asn Leu Val Gly Ala Ser
            20                  25                  30

Thr Ile Pro Met Gly Cys Ala Val Leu Pro Ser Leu Phe Tyr Leu Tyr
        35                  40                  45

Ser

<210> SEQ ID NO 36
<211> LENGTH: 37
<212> TYPE: PRT
<213> ORGANISM: Caenorhabditis elegans

<400> SEQUENCE: 36

Lys Lys Ala Ile Ser Ser Lys Phe Ala Leu Ile Asn Leu Met Lys Gly
1               5                   10                  15

Met Leu Gly Ala Gly Cys Phe Ser Val Pro Leu Ala Phe Lys Gln Ser
            20                  25                  30

```
Gly Tyr Val Ser Gly
        35

<210> SEQ ID NO 37
<211> LENGTH: 90
<212> TYPE: PRT
<213> ORGANISM: Caenorhabditis elegans

<400> SEQUENCE: 37

Thr Asp Leu Met Gly Ile Val Ser Ala Ala Gly Thr Ile Leu Tyr Ala
1               5                   10                  15

Leu Glu Gly Gln Ala Met Val Leu Pro Leu Glu Asn Arg Met Lys Lys
            20                  25                  30

Pro Glu Asp Met Lys Gly Pro Phe Gly Val Leu Ser Val Gly Val Gly
        35                  40                  45

Met Val Val Ile Tyr Ser Phe Ala Gly Phe Phe Gly Phe Leu Thr
    50                  55                  60

Tyr Gly Asn Asp Val Gln Asp Ser Ile Thr Leu Asn Leu Pro Asn Asp
65                  70                  75                  80

His Leu Gly Ile Phe Val Lys Ala Val Leu
            85                  90

<210> SEQ ID NO 38
<211> LENGTH: 49
<212> TYPE: PRT
<213> ORGANISM: Caenorhabditis elegans

<400> SEQUENCE: 38

His Phe Ala Phe Arg Tyr Ser Ile Val Ile Val Phe Leu Leu Ser
1               5                   10                  15

Tyr Ala Ile Pro Arg Leu Ser Asp Met Val Pro Leu Val Gly Val Thr
            20                  25                  30

Ala Gly Met Leu Leu Ala Leu Val Phe Pro Ser Leu Phe His Leu Leu
        35                  40                  45

Ile

<210> SEQ ID NO 39
<211> LENGTH: 37
<212> TYPE: PRT
<213> ORGANISM: Caenorhabditis elegans

<400> SEQUENCE: 39

Gly Asp Val Ile Thr Pro Thr Arg Ala Val Leu Thr Leu Ser Lys Ser
1               5                   10                  15

Met Phe Asn Ala Gly Cys Phe Ser Leu Pro Tyr Ala Trp Lys Leu Gly
            20                  25                  30

Gly Leu Trp Val Ser
        35

<210> SEQ ID NO 40
<211> LENGTH: 90
<212> TYPE: PRT
<213> ORGANISM: Caenorhabditis elegans

<400> SEQUENCE: 40

Thr Asn Phe Thr Gly Thr Ile Thr Met Ile Gly Met Ser Met Tyr Ala
1               5                   10                  15

Phe Glu Gly Gln Thr Met Ile Leu Pro Ile Glu Asn Lys Leu Asp Asn
            20                  25                  30
```

```
Pro Ala Ala Phe Leu Ala Pro Phe Gly Val Leu Ser Thr Thr Met Ile
            35                  40                  45

Ile Cys Thr Ala Phe Met Thr Ala Leu Gly Phe Phe Gly Tyr Thr Gly
 50                  55                  60

Phe Gly Asp Ser Ile Ala Pro Thr Ile Thr Thr Asn Val Pro Lys Glu
 65                  70                  75                  80

Gly Leu Tyr Ser Thr Val Asn Val Phe Leu
                85                  90

<210> SEQ ID NO 41
<211> LENGTH: 48
<212> TYPE: PRT
<213> ORGANISM: Caenorhabditis elegans

<400> SEQUENCE: 41

Asp Lys Gly Phe Arg Val Phe Trp Val Leu Val Thr Tyr Leu Met Ala
  1               5                  10                  15

Val Leu Ile Pro Lys Leu Glu Ile Met Ile Pro Leu Val Gly Val Thr
                20                  25                  30

Ser Gly Ala Leu Cys Ala Leu Ile Phe Pro Pro Phe Phe Glu Met Ile
            35                  40                  45

<210> SEQ ID NO 42
<211> LENGTH: 37
<212> TYPE: PRT
<213> ORGANISM: Caenorhabditis elegans

<400> SEQUENCE: 42

Glu Lys Gly Ile Gly Trp Ile Ile Gly Ala Ile Phe Ile Ile Gly Glu
  1               5                  10                  15

Thr Ala Gly Gly Gly Met Ile Ala Leu Ser Tyr Ala Leu Thr Ser Met
                20                  25                  30

Gly Leu Ile Pro Gly
            35

<210> SEQ ID NO 43
<211> LENGTH: 86
<212> TYPE: PRT
<213> ORGANISM: Caenorhabditis elegans

<400> SEQUENCE: 43

Asn Leu Leu Lys Ala Phe Met Ala Phe Gly Thr Phe Val Phe Ala Phe
  1               5                  10                  15

Gly Gly His Ala Thr Leu Pro Thr Ile Gln His Asp Met Lys Lys Pro
                20                  25                  30

Ala His Phe Val His Ser Val Leu Ala Ile Ile Phe Cys Thr Met
            35                  40                  45

Leu Tyr Met Cys Ile Ala Val Gly Gly Tyr Phe Val Tyr Gly Ser Thr
 50                  55                  60

Val Gly Glu Ala Ile Ile Pro Ser Leu Gln Ile Lys Trp Ile Gln Gln
 65                  70                  75                  80

Thr Val Asn Leu Met Ile
                85

<210> SEQ ID NO 44
<211> LENGTH: 49
<212> TYPE: PRT
<213> ORGANISM: Caenorhabditis elegans

<400> SEQUENCE: 44
```

```
Arg Phe Leu Val Arg Ser Ile Leu Phe Trp Phe Val Ile Phe Ile Gly
1               5                   10                  15

Leu Ser Ile Pro His Phe Gly Pro Val Leu Asp Leu Ile Gly Ala Ser
            20                  25                  30

Thr Met Val Leu Met Thr Leu Ile Leu Pro Pro Ile Phe Tyr Leu Ser
        35                  40                  45

Ile

<210> SEQ ID NO 45
<211> LENGTH: 37
<212> TYPE: PRT
<213> ORGANISM: Saccharomyces cerevisae

<400> SEQUENCE: 45

Ala Gly Gln Ser Thr Ala Pro Gln Thr Ile Phe Asn Ser Ile Asn Val
1               5                   10                  15

Leu Ile Gly Ile Gly Leu Leu Ala Leu Pro Leu Gly Leu Lys Tyr Ala
            20                  25                  30

Gly Trp Val Ile Gly
        35

<210> SEQ ID NO 46
<211> LENGTH: 87
<212> TYPE: PRT
<213> ORGANISM: Saccharomyces cerevisae

<400> SEQUENCE: 46

Ile Asp Leu Lys His Leu Cys Leu Ser Ile Gly Leu Leu Ser Ala Cys
1               5                   10                  15

Trp Gly Gly His Ala Val Phe Pro Asn Leu Lys Thr Asp Met Arg His
            20                  25                  30

Pro Asp Lys Phe Lys Asp Cys Leu Lys Thr Thr Tyr Lys Ile Thr Ser
        35                  40                  45

Val Thr Asp Ile Gly Thr Ala Val Ile Gly Phe Leu Met Phe Gly Asn
    50                  55                  60

Leu Val Lys Asp Glu Ile Thr Lys Asn Val Leu Leu Thr Glu Gly Tyr
65                  70                  75                  80

Pro Lys Phe Val Tyr Gly Leu
                85

<210> SEQ ID NO 47
<211> LENGTH: 49
<212> TYPE: PRT
<213> ORGANISM: Saccharomyces cerevisae

<400> SEQUENCE: 47

Gln Val Phe Asn Arg Ile Phe Ile Asn Val Val Phe Val Leu Ile Ala
1               5                   10                  15

Ile Asn Phe Pro Glu Phe Asp Lys Ile Ile Ala Phe Leu Gly Ala Gly
            20                  25                  30

Leu Cys Phe Thr Ile Cys Leu Ile Leu Pro Cys Trp Phe Tyr Leu Arg
        35                  40                  45

Leu

<210> SEQ ID NO 48
<211> LENGTH: 37
<212> TYPE: PRT
<213> ORGANISM: Arabidopsis thaliana
```

```
<400> SEQUENCE: 48

Lys Arg Thr Gly Thr Val Trp Thr Ala Ser Ala His Ile Ile Thr Ala
1               5                   10                  15

Val Ile Gly Ser Gly Val Leu Ser Leu Ala Trp Ala Val Ala Gln Ile
                20                  25                  30

Gly Trp Ile Gly Gly
            35

<210> SEQ ID NO 49
<211> LENGTH: 88
<212> TYPE: PRT
<213> ORGANISM: Arabidopsis thaliana

<400> SEQUENCE: 49

Gln Lys Ile Trp Arg Thr Phe Gln Ser Leu Gly Asn Ile Ala Phe Ala
1               5                   10                  15

Tyr Ser Tyr Ser Met Ile Leu Ile Glu Ile Gln Asp Thr Val Lys Ser
                20                  25                  30

Pro Pro Ala Glu Val Asn Thr Met Arg Lys Ala Thr Phe Val Ser Val
            35                  40                  45

Ala Val Thr Thr Val Phe Tyr Met Leu Cys Gly Cys Val Gly Tyr Ala
        50                  55                  60

Ala Phe Gly Asp Asn Ala Pro Gly Asn Leu Leu Ala His Gly Gly Phe
65                  70                  75                  80

Arg Asn Pro Tyr Trp Leu Leu Asp
                85

<210> SEQ ID NO 50
<211> LENGTH: 49
<212> TYPE: PRT
<213> ORGANISM: Arabidopsis thaliana

<400> SEQUENCE: 50

Arg Leu Val Trp Arg Thr Phe Phe Val Ile Thr Thr Thr Leu Ile Ser
1               5                   10                  15

Met Leu Met Pro Phe Phe Asn Asp Val Val Gly Leu Leu Gly Ala Ile
                20                  25                  30

Gly Phe Trp Pro Leu Thr Val Tyr Phe Pro Val Glu Met Tyr Ile Ala
            35                  40                  45

Gln
```

VESICULAR AMINO ACID TRANSPORTER COMPOSITION AND METHOD

This application claims priority to U.S. Provisional Application Serial No. 60/063,012, filed on Oct. 23, 1997, which is hereby incorporated by reference.

This invention was made with monetary support of Federal research grant 2 PO1 NS16033 from the NINDS. Accordingly, the United States government has certain rights in this invention.

FIELD OF THE INVENTION

The invention relates to amino acid transporter molecules useful in the diagnosis and treatment of disorders of the central and peripheral nervous systems.

REFERENCES

Alfonso, A., et al., *Science* 261:617–619 (1993).
Ausubel, F. M., et al., in *Current Protocols in Molecular Biology*, John Wiley and Sons, Inc., Media, Pa. (1988).
Brenner, S., *Genetics* 77:71–94 (1974).
Burger, P. M., et al., *Neuron* 7:287–293 (1991).
Chalfie, M., et al., *Science* 263:802–805 (1994).
Christensen, H., et al., *Eur. J. Pharmacol.* 207:73–79 (1991).
Clark, S. G., et al., *Genetics* 137:987–997 (1994).
Erickson, J. D., et al., *Proc. Natl. Acad. Sci. USA* 89:10993–10997 (1992).
Ferguson, E. L., and Horvitz, H. R., *Genetics* 110:17–72 (1985).
Fischer, W. N., et al., *J. Biol. Chem.* 270:16315–16320 (1995).
Fykse, E. M., and Fonnum, F., *J. Neurochem.* 50:1237–1242 (1988).
Hall, D. H., and Hedgecock, E. M. *Cell* 65:837–847 (1991).
Hell, J. W., et al., *EMBO J.* 7:3023–3029 (1988).
Harlow, E., et al., *Antibodies: A Laboratory Manual*, Cold Spring Harbor Lab (1988).
Jorgensen, E. M., et al., *Nature* 378:196–199 (1995).
Kish, P. E., et al., *Proc. Natl. Acad. Sci. USA* 86:3877–3881 (1989).
Liu, Q-R, et al., *Proc. Natl. Acad. Sci. USA* 89: 6639–6643 (1992a).
Liu, Y., et al., *Cell* 70:539–551 (1992b).
Liu, Y., et al., *J. Cell Biol.* 127:1419–1433 (1994).
Liu, Y., and Edwards, R. H., *Ann. Rev. Neurosci.* 20:125–156 (1997).
McElver, M. B., et al., *Anesthesiology* 84(4): 823–834, (1996).
McIntire, S., et al., *Nature* 364:337–341 (1993).
Nonet, M. L., et al., *Cell* 73:1291–1306 (1993).
Nonet, M. L., et al., *J. Neuroscience*, in press (1997).
Schuldiner, S., et al., *Physiol. Rev.* 75:369–392 (1995).
Thomas-Reetz, A., et al., *Proc. Natl. Acad. Sci. USA* 90:5317–5321 (1993).
Wilson, R., et al., *Nature* 368:32–38 (1994).

BACKGROUND OF THE INVENTION

Synaptic transmission in the central and peripheral nervous systems involves the regulated release from presynaptic terminals (exocytosis) of vesicles filled with neurotransmitter. Classical adrenergic and cholinergic neurotransmitters are synthesized in the cytoplasm and transported into the vesicles by active transport mechanisms in which intravesicular $H^+$ ions are exchanged for cytoplasmic transmitter.

Vesicular transport proteins for acetylcholine (ACh) and monamines have been characterized and are known in the art. Transport of these molecules depends primarily on the chemical component ($\Delta pH$) of the electrochemical gradient, $\Delta F_{H+}$. Molecular cloning has also demonstrated that the vesicular monoamine and ACh transporters are closely related in structure (Liu, 1992b; Erickson, et al., 1993; Alfonso, et al., 1993).

In contrast, it is now recognized that vesicular transport of the amino acid neurotransmitter glutamate depends primarily on the electrical component ($\Delta\Psi$) of $\Delta F_{H+}$, while vesicular GABA transport appears to depend more equally on both $\Delta pH$ and $\Delta\Psi$. In studies carried out in support of the present invention, attempts to identify additional members of the vesicular monoamine and ACh transporter family, including low stringency hybridization, polymerase chain reaction (PCR) amplification of the conserved domains using degenerate oligonucleotide primers, and search of the available databases have not yielded additional members capable of transporting amino acid transport, suggesting that the proteins which effect vesicular amino acid transport may be structurally quite different from those that transport the classical transmitters.

Amino acid neurotransmitters are now recognized to play important roles in neurotransmission and neuromodulation in the central and peripheral nervous systems of vertebrate, as well as in invertebrate, species. For example, enhancement of gamma-aminobutyric acid (GABA) transmission is associated with a number of activities, including, but not limited to anticonvulsant and sedative-hypnotic activities in the mammalian and muscle relaxation. Likewise, glycine is an inhibitory neurotransmitter, and enhancement of glycine transmission may result in anticonvulsive activity in the central nervous system. In contrast, the excitatory amino acid neurotransmitters glutamate and aspartate are proconvulsive; consequently, interference with glutamate or aspartate-mediated transmission may provide anticonvulsant effects and/ori CNS depression (McElver, et al., 1996).

Drugs which either enhance or inhibit uptake of the classical neurotransmitters into vesicles are known to provide useful therapeutic effects. It would be useful to identify similar drugs which affect amino acid transmitters via vesicular regulatory mechanisms. The present invention identifies a family of neuronal amino acid neurotransmitter transporters that effect loading of synaptic vesicles. According to an important aspect of the present invention, these transporters are sufficiently dissimilar from known monoamine or cholinergic transport proteins to define a new family of transporter proteins. These and other aspects of the invention are described herein.

SUMMARY OF THE INVENTION

According to one aspect, the invention is directed to a novel family of amino acid synaptic vesicle transporter proteins, exemplified by proteins having amino acid sequences which have substantial sequence identity to a protein having the sequence designated herein as UNC-47 and provided as SEQ ID NO: 1.

According to a related feature, the invention includes an isolated amino acid synaptic vesicle transporter protein which contains at least 10 putative transmembrane domain regions, each region having substantial sequence identity to at least one of transmembrane domain regions selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. According to an important feature of the invention, these transmembrane domains are highly conserved in members of the synaptic vesicle amino acid transporter protein described by the present invention. In a preferred embodiment, the amino acid sequence of the transporter protein of the invention is substantially identical to the transporter protein amino acid sequence designated herein as RUNC-47 and provided as SEQ ID NO: 2.

In one aspect, the invention provides an isolated nucleic acid encoding an amino acid synaptic vesicle transporter protein as exemplified by the coding regions of UNC-47 and RUNC-47 (SEQ ID NO:3 and SEQ ID NO:4, respectively), or is complementary to such an encoding nucleic acid sequence, and remains stably bound to it under at least moderate, and optionally, under high stringency conditions.

According to a related embodiment, the invention includes isolated DNA fragments that encode the synaptic vesicle amino acid transporter proteins described above. According to an important feature, such fragments include a 3' untranslated region, having substantial sequence identity to the 3' untranslated region presented in SEQ ID NO: 4.

The invention also includes recombinant expression vectors that encompass the DNA fragments just described, as well as recombinant cells transfected with such vectors. The invention further includes antibodies directed to the proteins described above.

In yet another related aspect, the present invention includes methods of identifying a candidate compound capable of modulating amino acid transport into synaptic vesicles in the nervous system. According to this aspect of the invention, the method includes the steps of: (a) contacting a test compound with a transporter protein with an amino acid sequence which is substantially identical to SEQ ID NO: 2, under conditions in which the activity of the transporter protein can be measured; (b) measuring the effect of the test compound on the activity of such transporter protein; and (c) selecting the test compound as a candidate compound if its effect on the activity of the transporter protein is above a selected threshold level.

According to a preferred embodiment, this method is carried out in the membrane of a recombinant eukaryotic cell (i) transfected with a recombinant expression vector, comprising e.g., a DNA fragment encoding an amino acid synaptic vesicle transporter protein with an amino acid sequence which is substantially identical to SEQ ID NO: 2 or fragments thereof, which is operably linked to a regulatory sequence capable of promoting expression of the protein in a selected host, and (ii) capable of expressing the protein and processing the transporter protein for incorporation into the cell membrane. Generally, synaptic vesicle uptake of the selected neurotransmitter is measured in such an assay.

In still another related aspect the invention is directed to treatment methods, for example, treatment for a neuropsychiatric condition characterized by neuronal deficiency of GABA. According to this aspect, a subject is given a pharmaceutically effective amount of a compound capable of enhancing amino acid transport into synaptic vesicles via a transporter protein characterized by substantial sequence identity to SEQ ID NO: 2.

These and other objects and features of the invention will become more fully apparent when the following detailed description of the invention is read in conjunction with the accompanying drawings.

BRIEF DESCRIPTION OF THE DRAWINGS

FIGS. 1A and B show the sequence and structure of vesicular GABA transporters UNC-47 (SEQ ID NO: 1) derived from C. elegans and rat UNC-47 homolog (RUNC-47; SEQ ID NO: 2) derived from rat, where underlining indicates predicted transmembrane domains (designated TM1-10) (SEQ ID NOS 5–14, corresponding to RUNC-47 TM1-TM10, and SEQ ID NOs: 15–24, corresponding to UNC-47 TM1-TM10, respectively;

FIG. 2 shows the predicted secondary structure of the rat unc-47 homologue with the lumen of the vesicle shown above and the cytoplasm below, where a minus sign (−) represents acidic residues and a plus sign (+) represents basic residues, filled circles indicate residues identical (black) or highly conserved (speckled) with UNC-47, and unfilled circles indicate divergent residues;

FIG. 3 shows unc-47 mutations (SEQ ID NO: 31–32) induced by ethyl methanesulphonate (EMS);

FIG. 4 shows a comparison of UNC-47 (SEQ ID NO: 1) to representative protein sequences from C. elegans [F2112.3 (U23518) (SEQ ID NO: 33–35), C44B7.6 (U28928) (SEQ ID NO: 36–38), F59B2.2 (P34479) (SEQ ID NO: 39–41), R02F2.8 (U00055) (SEQ ID NO: 42–44)], S. cerevisiae [YJR001w (P47082) (SEQ ID NO: 45–47)], and plants [amino acid permease AAP5 (S51170) (SEQ ID NO: 48–50) from Arabidopsis thalania], showing three colinear regions of highest sequence identity to UNC-47, where residue position in the sequences of the polypeptides are indicated in parentheses and where residues identical in three or more of the proteins are shown in black and similar residues in gray, as defined by Blast Blossum62 matrix analysis (The percent amino acid identity between UNC-47 and related proteins for each region is shown to the right. The F59B2.2 sequence includes a conserved domain that was present in genomic DNA but not predicted by Genefinder);

FIGS. 8A–8L show in situ hybridization of expression of rat unc-47 homolog in GABAergic cell populations (FIGS. 8A–8L), $^{35}$S-labelled anti-sense RNA probes for GAD-67 (FIGS. 8A,8D,8G,8J), the rat unc-47 homologue (RUNC; FIGS. 8B,8E,8H,8K), and a sense probe for RUNC (FIGS. 8C,8F,8I,8L) were hybridized with sections through the basal ganglia (FIGS. 8A–8C), thalamus (FIGS. 8D–8F), cerebellum (FIGS. 8G–8I), spinal cord (FIGS. 8J–8L), where Cx indicates cortex, CPu the caudate-putamen, S the septal nuclei, Hc the hippocampus, Pt the pretectal nuclei, Rt the reticular nucleus of the thalamus, ZI the zona incerta, Hy the hypothalamus, p the purkinje cell layer of the cerebellum, m the molecular layer, g the granule cell layer, DH the dorsal horn of the spinal cord and VH the ventral horn, and where bars indicate 1 mm and the bar in FIG. 8A applies to FIGS. 8A–8I, the bar in FIG. 8J to FIGS. 8J–8L;

FIGS. 9A and 9B show brain sections from hippocampus (A) and cerebellum (B) hybridized with $^{35}$S-labelled anti-sense RNA for the unc-47 homologue, then counter-stained with cresyl violet and viewed under darkfield illumination, showing hippocampal regions hilus of the dentate gyrus (DG), regions CA1 and CA3, and cerebellar Purkinje cell (p), molecular (m) and granule cell (g) layers;

FIGS. 10A and 10B show double immunofluorescence of primary hippocampal cultures for the unc-47 homologue (A) coinciding with immunoreactivity for synaptophysin (B);

DETAILED DESCRIPTION OF THE INVENTION

I. Definitions

Figure 5A:
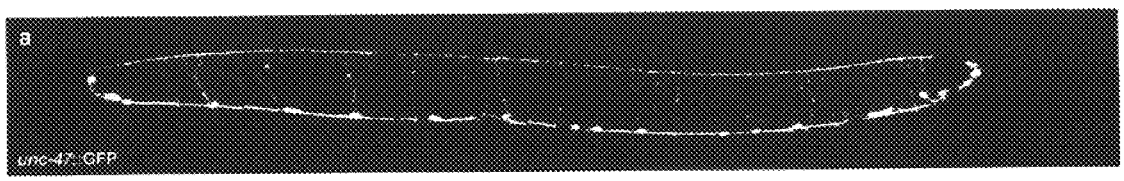
FIGS. 5A and 5B show a computer-generated confocal image of an adult C. elegans oxIn12 containing an integrated array of unc-47:GFP reporter construct (A), and a camera lucid depiction of the worm showing the distribution of GABAergic neurons (B)

Unless otherwise indicated, all terms used herein have the same meaning as they would to one skilled in the art of the present invention. Practitioners are particularly directed to *Current Protocols in Molecular Biology* (Ausubel, et al., 1988) for definitions and terms of the art.

The term "synaptic vesicle transporter protein" as used herein refers to a membrane protein that is capable of effecting the passage of a selected neurotransmitter or neurotransmitters into a synaptic vesicle, usually in an energy dependent manner. Such transport activity can be measured in vitro, for example, using the methods described in Example 8 herein.

The term "amino acid neurotransmitter" refers to molecules that are amino acids or are derived from amino acids and which are known modulators or effectors of neurotransmission in the central or peripheral nervous system. Examples of amino acid neurotransmitters include, but are not limited to GABA, glycine, aspartate, taurine, and glutamate.

The terms "heterologous DNA" and "heterologous RNA" refer to nucleotides that are not endogenous to the cell or part of the genome in which they are present; generally such nucleotides have been added to the cell, by transfection, microinjection, electroporation, or the like. Such nucleotides generally include at least one coding sequence, but this coding sequence need not be expressed.

As used herein, the terms "substantial homology", "substantial similarity", or "substantial identity", and declinations thereof, refer to concordance of one amino acid sequence with another amino acid sequence or of one polynucleotide sequence with another polynucleotide sequence when such sequences are arranged in a best fit alignment, as further defined below.

The term "polynucleotide" as used herein refers to a polymeric molecule having a backbone that supports bases capable of hydrogen bonding to typical polynucleotides, where the polymer backbone presents the bases in a manner to permit such hydrogen bonding in a sequence specific fashion between the polymeric molecule and a typical polynucleotide (e.g., single-stranded DNA). Such bases are typically inosine, adenosine, guanosine, cytosine, uracil and thymidine. Polymeric molecules include double and single stranded RNA and DNA, and backbone modifications thereof, for example, methylphosphonate linkages.

The term "high stringency conditions" as used herein refers to hybridization conditions as provided in Maniatis, et al., *Molecular Cloning: A. Laboratory Manual*, 2d. Edition (1989), hereby incorporated by reference. An example of "high stringency" conditions includes hybridization at about 65° C. in about 5×SSPE and washing at about 65° C. in about 0.1×SSPE (where 1×SSPE=0.15 sodium chloride, 0.010 M sodium phosphate, and 0.001 M disodium EDTA).

The term "vector" or "expression vector" refers to a nucleotide sequence that can assimilate new nucleic acids, and propagate those new sequences in an appropriate host. Vectors include, but are not limited to recombinant plasmids and viruses. The vector (e.g., plasmid or recombinant virus) comprising the nucleic acid of the invention can be in a carrier, for example, a plasmid complexed to protein, a plasmid complexed with lipid-based nucleic acid transduction systems, or other non-viral carrier systems.

The term "expression vector" refers to vectors that have the ability to incorporate and express heterologous DNA fragments in a foreign cell. Many prokaryotic and eukaryotic expression vectors are commercially available. Selection of appropriate expression vectors is within the knowledge of those having skill in the art.

Two nucleic acid elements or fragments are said to be "heterologous" if the elements are derived from two different genes, or alternatively, two different species.

The term "polypeptide" as used herein refers to a compound made up of a single chain of amino acid residues linked by peptide bonds. The term "protein" may be synonymous with the term "polypeptide" or may refer, in addition to a complex of two or more polypeptides.

The term "splice variant" refers to a protein that is coded by a common gene but which has a sequence that is altered due to alternative splicing of the mRNA prior to translation.

An "expressed sequence tag" or EST is a short (typically 200–300) bp segment derived from a cDNA sequence, whose sequence is unique, as evidenced by ability to be selectively amplified using specific primers in a polymerase chain reaction. It is a sequence known to be expressed (i.e., at least transcribed and most likely translated). ESTs can be used to create an "expression" map by adding the locations of the genes themselves to the physical maps.

The term "cosmid vector" refers to a recombinant plasmid that contains inserted fragments of up to about 45–50 kb in length which can be introduced into cells of *E. coli*. Generally, a cosmid vector consists of a COS sequence from λ-page DNA into a small *E. coli* vector about 5 kb long. Cosmid vectors are generally used to introduce larger sequences into a cell than is possible using conventional plasmid vectors.

Amino acid residues are referred to herein by their standard single letter notations: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; X, hydroxyproline; Y, tyrosine.

II. Amino Acid Synaptic Vesicle Transporter Proteins

As mentioned above, a number of amino acid neurotransmitters are now known to be important effectors of neurotransmission in the central and peripheral nervous systems of vertebrate, as well as of invertebrate forms of life. It is now appreciated that such transmitters share many of the regulatory mechanisms generally associated with the so-called classical transmitters (adrenergic and cholingeric systems). Particularly pertinent to the present invention is the vesicular uptake system present in pre-synaptic nerve terminals which provides a supply of vesicular transmitter that is ready for release into the synaptic cleft in response to a nerve impulse. Blockade of such a transport system results in a diminished supply of vesicular transporter, while enhancement of transport into vesicles may result in an increased outflow of neurotransmitter in response to a nerve stimulus.

While a number of amino acid transport proteins have been previously identified, none has been shown to be a vesicular transporter. For example, Liu, et al., (1992a) described a GABA transporter protein having homology to certain invertebrate proteins, including one from C. elegans. However, this transporter molecule is located on the plasma membrane of the presynaptic nerve cell and effects re-uptake of the transmitter into the presynaptic nerve terminal (i.e., effecting transport across the cell plasma membrane into the cell, as opposed to transport from the cell cytoplasm into the vesicle). Similarly, U.S. Pat. No. 5,658,786 describes GABA and taurine transport molecules that may form part of the synaptic cleft-plasma membrane re-uptake system. These sequences exhibit no appreciable or minimal sequence identity to the family of synaptic vesicle transporter proteins that form the basis of the present invention.

According to an important feature of the present invention, while a number of cholinergic and adrenergic synaptic vesicle transporter proteins have been identified and sequenced, attempts to identify additional members of the vesicular monoamine and ACh transporter family, including low stringency hybridization, polymerase chain reaction (PCR) amplification of the conserved domains using degenerate oligonucleotide primers, and search of the available databases have not yielded additional members. These studies indicate that the proteins that effect vesicular amino acid transport may have distinct sequences.

This section describes the identification and isolation from invertebrate and vertebrate species of specific amino acid neurotransmitter vesicular transporter proteins. Exemplified herein is isolation of a GABA vesicular transport protein; however, in accordance with the present invention, it is now appreciated that this protein is a member of a larger family of vesicular transport proteins that are sequentially interrelated and which effect transport of a number of neurotransmitter amino acids, and as exemplified herein by SEQ ID NO:1, SEQ ID NO:2, SEQ ID NO:26, and SEQ ID NO:28. Therefore, it is appreciated that the methods described herein may be used to identify and isolate heretofore unidentified amino acid vesicular transport proteins. Moreover, using the sequence information presented herein, persons of ordinary skill in the art will be able to identify additional family members, including, but not limited to vesicular transporter proteins from additional animal species and/or vesicular transporters that are specific for transporting other amino acid neurotransmitters, including, but not limited to glycine, glutamate, aspartate, and the other amino acid neurotransmitters.

A. Identification of GABA Synaptic Vesicle Transport Molecules

This section describes how synaptic vesicle transporter molecules of the invention can be identified in invertebrate species, and how vertebrate homologues can be further identified therefrom. Alternatively, or in addition, further vertebrate homologs can be identified using sequence information derived from the novel amino acid (GABA) vesicular transport molecules described below.

1. Identification of unc-47 Gene Product in C. elegans

The nematode worm *Caenorhabditis elegans* has 26 GABA expressing neurons that are required to inhibit contractions of the head muscles during foraging, to inhibit contractions of the body muscles during locomotion and to stimulate contraction of the enteric muscles during the defecation cycle. Animals in which the GABAergic neurons are ablated are defective in all three behaviors. Five genes have been identified that when mutated cause defects in these behaviors (McIntire, et al, 1993b). However, the phenotype of only one of these mutants, unc-47, is consistent with a loss of GABA transport into synaptic vesicles. First, the defect in unc-47 is global, affecting all of the behaviors mediated by GABA. Second, the defect in unc-47 is presynaptic since the muscle cells in the mutant respond normally to GABA receptor agonists. Third, GABA accumulates in GABAergic neurons of the mutant, suggesting that the neurotransmitter is not being released, possibly because it is not loaded into synaptic vesicles.

C. elegans unc-47 maps between stP127 and unc-50 on chromosome III, which has been fully sequenced and is known in the art (Wilson, et al., 1994). This region contains approximately 250 kilobases of DNA. Cosmids spanning this region were generated according to standard methods known in the art, and were injected into unc-47 mutant worms, as detailed in Example 1. Two cosmid clones derived from chromosome III, T20G5 and E03F9, each rescued the unc-47 mutant phenotype. The rescuing activity was further localized to a 5.2 kb BamHI genomic fragment which contains a single complete open reading frame (T20G5.6) predicted by the *C. elegans* Genome Project (Wilson, et al., 1994). To confirm that the identified open reading frame corresponds to the gene mutated in unc-47 animals, three ethyl methanesulfonate-induced alleles were sequenced, according to methods known in the art. The reference allele, e307 (Brenner, 1974) is a G to A transition of the absolutely conserved G in the splice acceptor site between exons five and six (FIG. 3). A second strong mutation, n2476, is a 238 base pair deletion which removes parts of exons three and four; this deletion causes a frameshift at residue 175 and the open reading frame terminates after another 115 amino acids indicating that this allele is a molecular null. Finally, n2409 is a G to A transition which changes a glycine to arginine at residue 462 in a predicted transmembrane segment.

2. Structural Characterization of unc-47 Gene Product

Figure 1A:
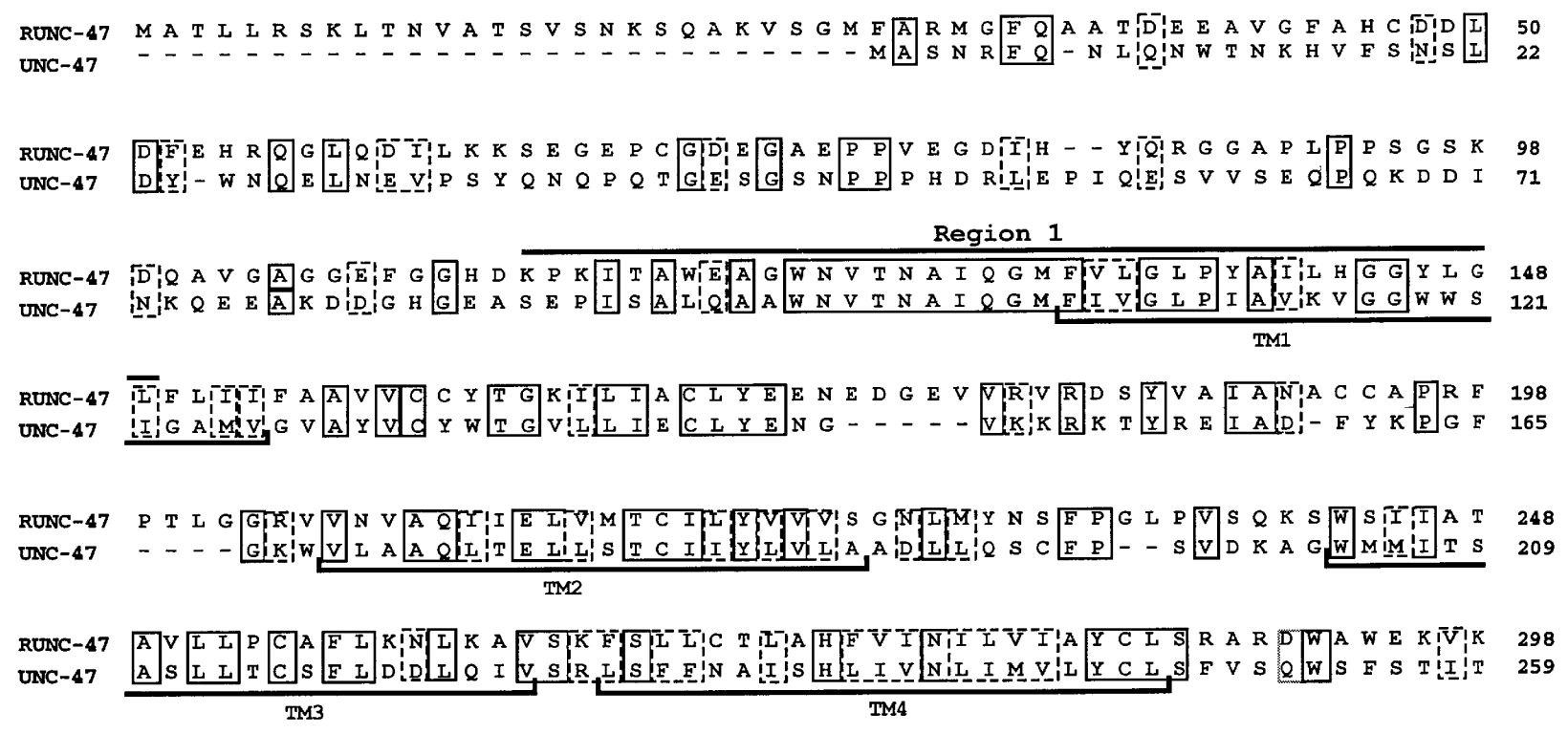

The cDNA derived from the unc-47 gene predicts a novel protein of 486 amino acids (SEQ ID NO: 1; FIG. 1) with no identity to the previously characterized vesicular monoamine and ACh transporters (Liu, et al., 1992b; Erickson et al, 1992). However, the predicted polypeptide expressed by the unc-47 DNA sequence includes ten transmembrane domains (TMDs), predicted on the basis of hydrophobicity analysis of the sequence, consistent with a membrane protein having a role in transport. In the diagram, the predicted transmembrane domains are underlined, and numbers in the right column correspond to amino acid residues. The conserved amino acid G (462), which is mutated in allele n2409, is indicated with an asterisk. Also shown in FIG. 1 is the rat homolog of UNC-47, RUNC-47 (SEQ ID NO: 2), isolated as described below. Black boxes indicate identical residues and gray boxes indicate conservative substitutions between UNC-47 and RUNC-47.

FIG. 2 shows a schematic of the predicted secondary structure of the rat unc-47 homologue (RUNC-47) of *C. elegans* unc-47 (see below) with the lumen of the vesicle shown above and the cytoplasm below. In the diagram, (−) represents acidic residues and (+) represents basic residues. The filled circles indicate residues identical (black) or highly conserved (gray) with UNC-47 and the unfilled circles indicate divergent residues.

Figure 4:
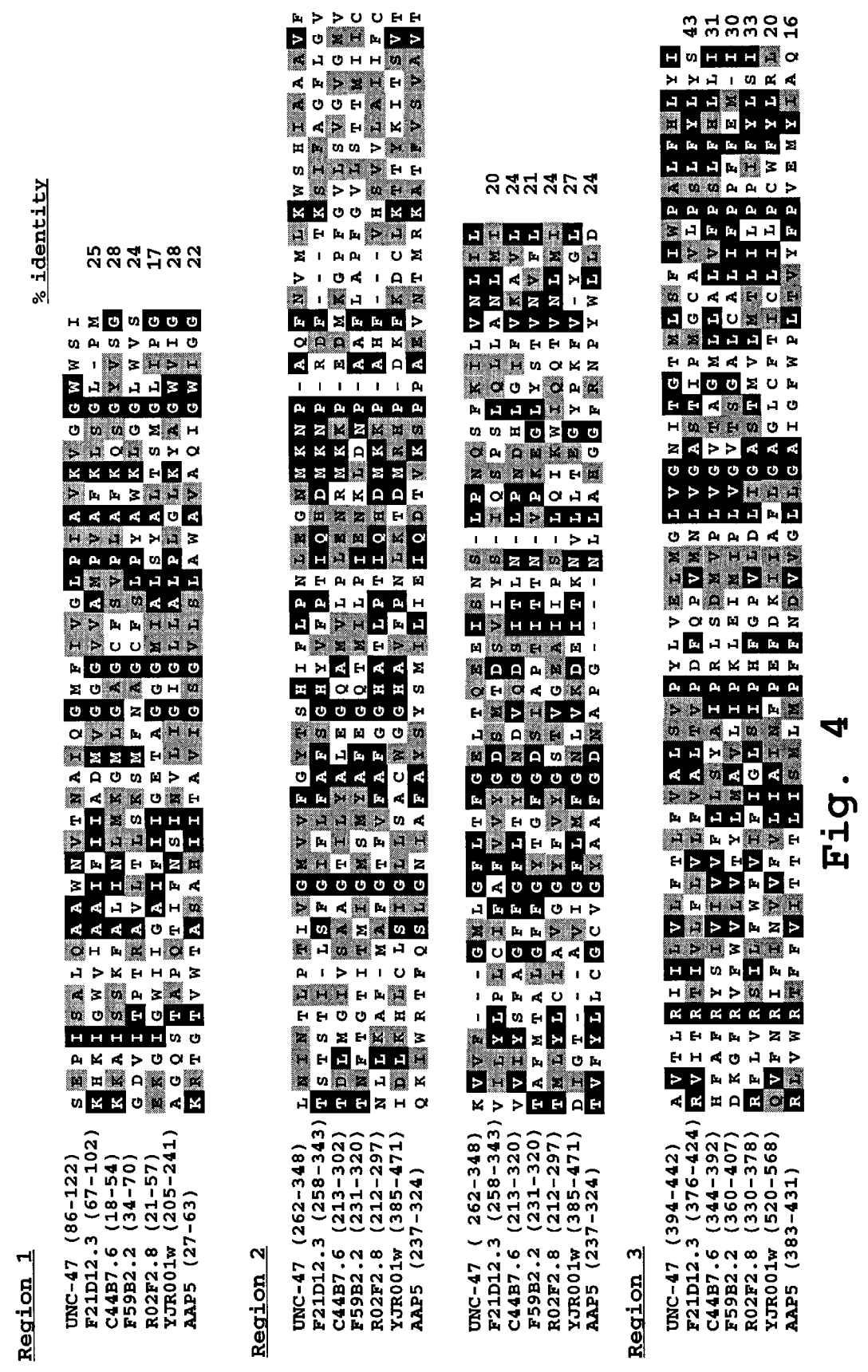

A search of available gene databases with the UNC-47 protein sequence revealed that UNC-47 has only a weak sequence identity to four predicted proteins in *C. elegans*, seven predicted proteins in *S. cerevisiae* and previously characterized amino acid permeases in *Arabidopsis thaliana* and *Nicotiana sylvestria* (FIG. 4). None of the referenced known proteins has been identified as a vesicular membrane transporter protein.

Figure 5B:
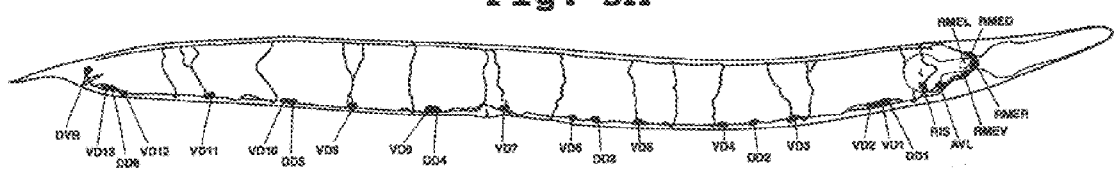

3. Characterization of Vesicular Transport Function of UNC-47 in *C. elegans* a. Localization to Synaptic Vesicles. To identify the cells that express unc-47, a marker construct of UNC-47 was constructed, as detailed in Example 2. Briefly, the protein coding sequence of green fluorescent protein (GFP; Chalfie, et al., 1994) was inserted in-frame 52 amino acids downstream of the UNC-47 translation start site and co-injected with a lin-15+ marker gene (Clark, et al, 1994) into lin-15 (n765ts) mutant animals (Ferguson and Horvitz, 1985). Animals containing the unc-47::GFP reporter construct showed expression of GFP in all GABAergic neurons and only in GABAergic neurons (FIGS. 5A and 5B), further supporting a role of the protein in GABA transport. To determine whether UNC-47 associates with synaptic vesicles, GFP was inserted at the carboxy terminus of the UNC-47 protein. This construct rescued the unc-47 mutant phenotype, demonstrating that the construct functions normally.

Figure 6A:
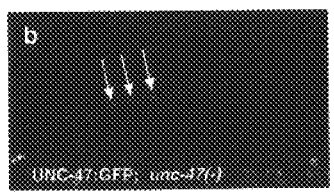
FIGS. 6A and 6B show computer-generated confocal images illustrating the distribution of GFP-tagged UNC-47 protein in a C. elegans unc-47 (e307) mutant (dorsal cord at posterior reflex of gonad) (A) and in an unc-104 (e1265) mutant (dorsal cord at posterior reflex of the gonad) (B)

In studies carried out in support of the present invention the unc-47(e307) mutant worm that contains an extrachromosomal array (oxEx68) of an UNC-47:GFP translational fusion construct was subjected to confocal imaging at the posterior reflex of the gonad. As shown in FIG. 6A, GFP-tagged UNC-47 protein was localized to synaptic varicosities along the ventral and dorsal cords but not in axons, similar to the distribution of other synaptic vesicle proteins such as synaptobrevin (Jorgensen, et al., 1995) synaptotagmin (Nonet, et al., 1993) and rab3a (Nonet, et al., 1997). The same distribution of UNC-47:GFP was observed in wild-type animals.

Figure 6B:
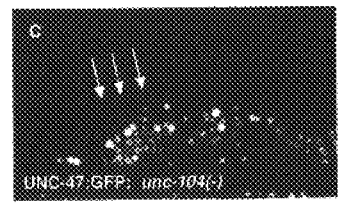

Further, mislocalization of synaptic vesicles in the unc-104 mutant (which lacks a neuron-specific kinesin; Hall and Hedgecock, 1991) also results in mislocalization of UNC-47, as revealed by confocal images of the dorsal cord at the posterior reflex of the gonad in an unc-104(e1265) mutant which contains an UNC-47:GFP translational fusion construct. In these mutants, synaptic vesicles do not reach the neuromuscular junction and accumulate in motor-neuron cell bodies (Jorgenson, et al., 1995). Similarly, in unc-104 mutants, GFP-tagged UNC-47 is present only in cell bodies and is not transported to the neuromuscular junction. As shown in FIG. 6B, GFP fluorescence was not observed at the nerve terminals of unc-104 mutants but was found only in the cell bodies. (Round spots in the image are autofluorescent gut granules and are not associated with GFP expression.)

Thus, the sequence, distribution and subcellular localization of UNC-47 is consistent with a role in the packaging of GABA into synaptic vesicles.

4. Isolation of Vertebrate Homologs of UNC-47

This section describes identification and isolation of vertebrate homologs of UNC-47. It is appreciated, in accordance with the present invention that the methods described herein can also be used to identify further members of the amino acid synaptic vesicle transporter proteins described herein.

Generally it is appreciated that further members of such family will preferably be substantially similar (i.e., exhibit at least about 70% sequence identity or homology) to either UNC-47, or the rat UNC-47 homolog, as described below.

Figure 1B:
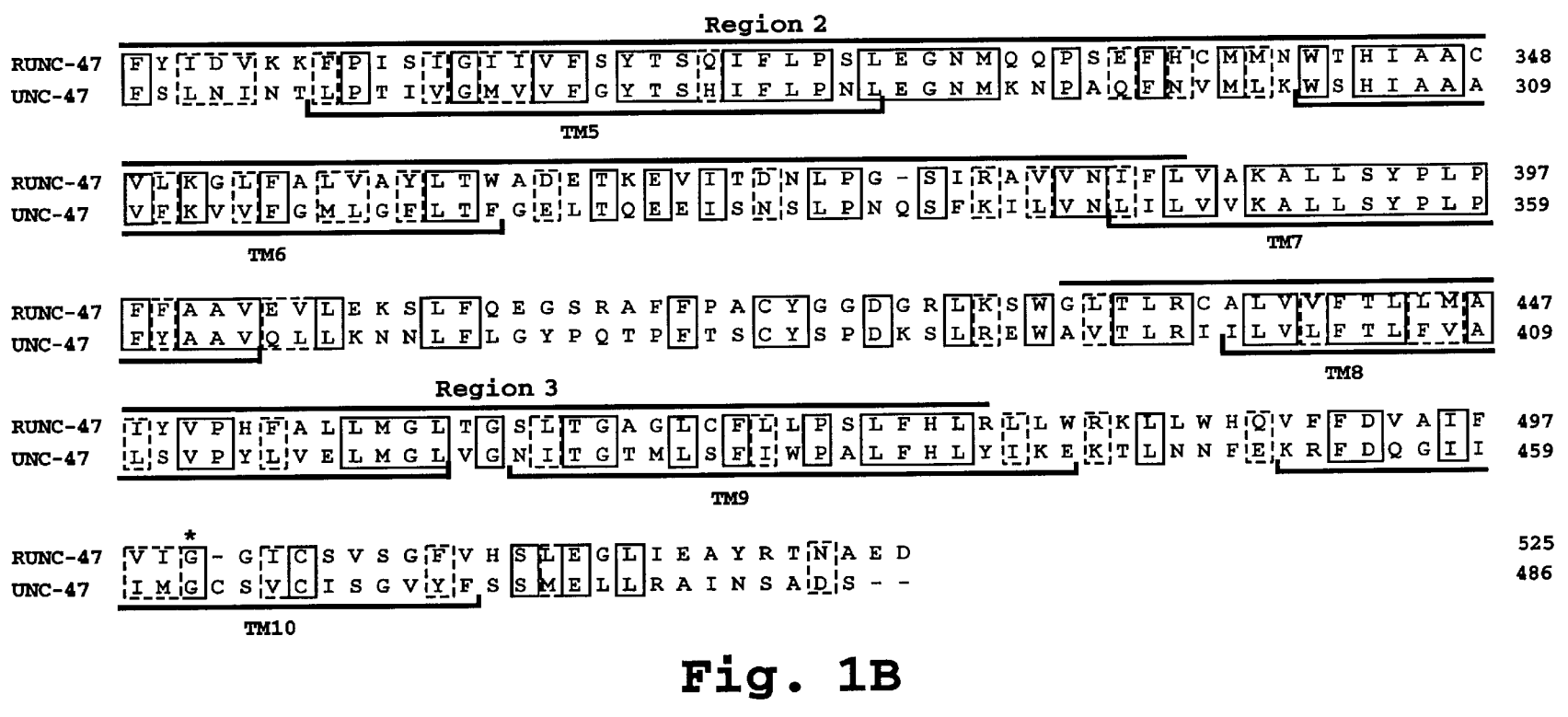

As used herein, a protein is an "amino acid synaptic vesicle transporter protein" if the amino acid sequence is greater than about 70% or 75%, preferably greater than about 80% or 85%, more preferably greater than about 90% and most preferably greater than 95% identical to the amino acid synaptic vesicle transporter protein amino acid sequence shown in FIGS. 1A and B (SEQ ID NO:1 and SEQ ID NO:2, for UNC-47 and RUNC-47, respectively). In some embodiments the identity will be as high as about 98%.

Further, it is appreciated that additional human or non-human members of the synaptic vesicle amino acid transport protein family defined herein will include at least 10 predicted or actual TMDs that are substantially similar to the TMDs present in RUNC-47 or UNC-47. Preferably, the relative locations of these TMDs in the homolog molecules will be constant with respect to the N- and C-termini of the molecule. Accordingly, as used herein, a protein is also an "amino acid synaptic vesicle transporter protein" if the amino acid sequence is greater than about 70% or 75%, preferably greater than about 80% or 85%, more preferably greater than about 90% and most preferably greater than 95% identical to the amino acid synaptic vesicle transporter protein transmembrane domains presented as SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, and SEQ ID NO: 24 for UNC-47 and SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14 for RUNC-47, respectively, of the amino acid sequence shown in FIGS. 1A and B (SEQ ID NO:1 and SEQ ID NO:2, for UNC-47 and RUNC-47, respectively).

Alignment for purposes of determining percent amino acid sequence identity can be achieved in various ways that are within the skill in the art, for instance, using publicly available computer software such as LALIGN, operated with default parameters. Sequence similarity and/or identity is determined using standard computer programs known in the art, such as BLAST, FASTA, or SSEARCH operated with default parameters [See, e.g., Altschul, et al., J. Mol. Biol., 215:403–410 (1990); Altschul, et al., Nucl. Acids Res 25(17) 3389–3402 (1997); Pearson, W R., Methods in Enzymology 266:227–258 (1996); Henikoff and Henikoff, Proc Nat Acad. Sci. 89:10915–10919 (1992)].

As used herein, a polynucleotide encoding an "amino acid synaptic vesicle transporter protein" may contain, for example, a coding sequence having at least about 70% or 75%, preferably greater than 80% or 85%, more preferably greater than about 90% and most preferably greater than 95% sequence identity to the coding region of the nucleic acid sequence of SEQ ID NO:3 or SEQ ID NO:4. In a specific embodiment, the nucleic acid sequence comprises a sequence substantially identical to the coding region of the nucleic acid sequence of SEQ ID NO:3 or SEQ ID NO:4.

The composition also contemplates fragments of the nucleic acid sequences presented as SEQ ID NO:3 or SEQ ID NO:4, at least about 20 nucleotides in length, preferably about 50 to 60 nucleotides in length, more preferably about 70 to 80 nucleotides in length and most preferably about 80 to 90 nucleotides in length. It will be appreciated that in some cases the composition contemplates fragments of the nucleic acid sequences presented as SEQ ID NO:3 or SEQ ID NO:4, that are greater than 90 nucleotides in length.

A determination of percent sequence identity for nucleic acid sequences may be done as described above for amino acid sequences are aligned using a sequence alignment program, as above. Corresponding poly nucleotide and polypeptide regions typically contain a similar, if not identical, number of residues. It will be understood, however, that corresponding regions may contain insertions or deletions of residues with respect to one another, as well as some differences in their sequences.

A database search with the predicted peptide sequence of unc-47 identified multiple entries in the mouse expressed sequence tag (EST) database. A fragment of one EST (identifier: 252177) was amplified by PCR and used to screen a mouse brain cDNA library. Partial sequence of a 2.5 kb cDNA showed strong identity to unc-47, as assessed by standard methods, and this cDNA was in turn used to screen a rat brain cDNA library. The resulting rat cDNA sequence contains a 3' untranslated region with approximately 95% sequence identity to mouse and human but not *C. elegans* sequences, a level exceeding that observed in much of the translated domain. According to a feature of the present invention, this region may be important to efficient recombinant expression of the molecule. The rat homolog DNA sequence (SEQ ID NO: 4) has been deposited in Genbank as accession number AF 030253, released concurrent to the priority filing date of the present application.

The sequence of the largest open reading frame predicts a novel protein of 525 amino acids with 35% identity and 63% similarity to unc-47, as shown in FIGS. 1A and B (RUNC-47). Similar to UNC-47, the analysis of hydrophobic moment predicts ten transmembrane domains (TMDs) and the absence of a signal peptide predicts that the amino and the carboxy termini reside in the cytoplasm (FIG. 2). In addition, the hydrophilic N-terminal domain is unusually large (approximately 132 residues). Consensus sequences for phosphorylation by protein kinase C occur on predicted cytoplasmic domains near the N-terminus (+17), between TMDs 2 and 3 (+239) and between TMDs 6 and 7 (+377) in RUNC-47.

Similar methods can be employed using human brain cDNA library to identify human homolog(s) of RUNC-47. In the context of the present invention, such identity (concordance of amino acid or coding sequence) may be assessed, for example, using a Mac Vector™ alignment program, or other programs described herein using default parameters according to methods known in the art.

Figure 7:
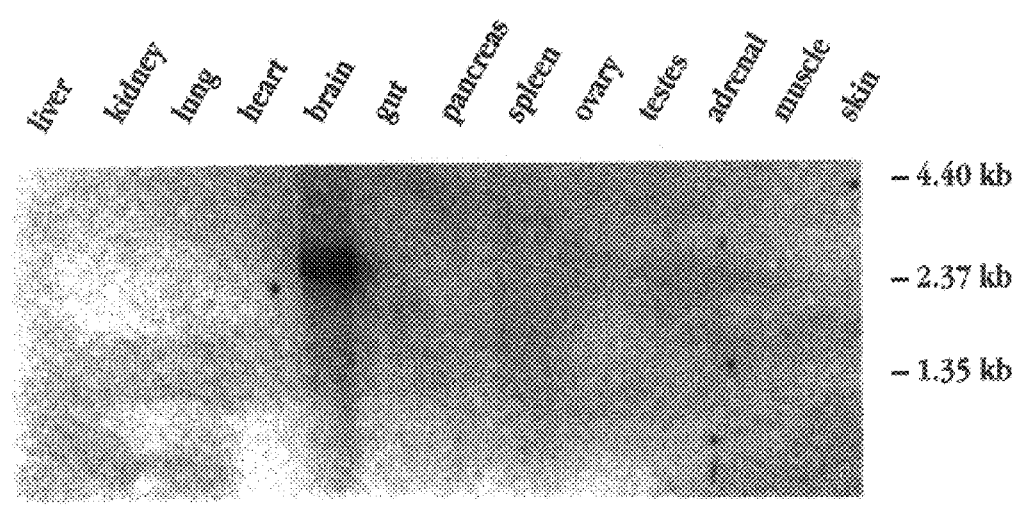
FIG. 7 shows Northern blots of poly-A+ RNA prepared from various tissues, using RUNC-47 (rat unc-47homolog) cDNA as probe.

5. Biochemical and Functional Characterization of RUNC-47 as a Vesicular Transporter Protein Tissue distribution of RUNC-47 was examined in order to further define its presynaptic function. Northern analysis carried out as detailed in Example 4 reveals expression of an approximately 2.5 kb mRNA transcript in the brain, with no RUNC-47 detected in non-neural tissues (FIG. 7). However, PCR amplification of reverse-transcribed sequences from spleen, testis and pancreas but not liver or kidney do indicate expression of the unc-47 homologue, consistent with detection of GABA biosynthesis and transport in some of these tissues (Thomas-Reetz, et al., 1993).

In situ hybridization was carried out as detailed in Example 5 to examine the pattern of expression of the unc-47 homologue throughout the neuraxis. In experiments carried out in support of the invention, specific and non-specific radiolabeled probes were contacted with various regions of the central nervous system. Thus, with reference to the panels indicated in FIGS. 8A–8L, $^{35}$S-labelled anti-sense RNA probes for GAD-67 (FIGS. 8A,8D,8G,8J), the rat unc-47 homologue (RUNC; FIGS. 8B,8E,8H,8K), and a sense probe for RUNC (FIGS. 8C,8F,8I,8L) were hybridized with sections through the basal ganglia (FIGS. 8A–8C), thalamus (FIGS. 8D–8F), cerebellum (FIGS. 8G–8I), spinal cord (FIGS. 8J–8L). The pattern of hybridization by the unc-47 homologue anti-sense probe appears identical to the anti-sense probe for GAD-67, with no significant hybridization by the sense probes for the unc-47 homologue or GAD-67 (not shown).

In summary, as shown in FIGS. 8A–8L, RUNC-47 is expressed at particularly high levels within the neocortex, hippocampus, cerebellum, striatum, septal nuclei and the reticular nucleus of the thalamus (FIGS. 8A–8L), regions containing abundant GABAergic neurons.

FIGS. 9A and 9B show high magnification of some of the foregoing autoradiograms. Examination of these images indicates expression by Purkinje cells of the cerebellum as well as by interneurons of the cerebellum, hippocampus (FIGS. 9A, 9B) and cortex, cell populations known to release GABA. In addition, in situ hybridization was performed with one isoform of the biosynthetic enzyme glutamic acid decarboxylase (GAD), GAD-67 (FIGS. 9A and 9B). Although the level of hybridization in different regions varied slightly between the unc-47 homologue and GAD-67, there is striking co-localization of the two sequences, consistent with a role for the unc-47 homologue in the release of GABA. The hippocampus (FIG. 9A) shows expression in the hilus of the dentate gyrus (DG) and regions CA1 and CA3. Minimal staining occurs in the granule cells of the DG and in pyramidal cells. The cerebellum (FIG. 9B) shows strong hybridization in the Purkinje cell (p) and molecular layers, with little hybridization in the granule cell layer (g). Hybridization with the GAD-67 probe shows a similar pattern and sense probes showed no signal (data not shown).

In further studies in support of the present invention, primary hippocampal cultures were stained with an antibody raised against the RUNC-47 protein homologue. FIGS. 10A and 10B show punctate immunoreactivity in nerve processes that coincides with the immunoreactivity for synaptophysin (arrows). (Synaptophysin immunoreactivity that does not co-localize with staining for RUNC-47 likely reflects the presence of non-GABAergic neurons in the culture.) The apparent vesicular localization of RUNC-47 further supports a role for the unc-47 homologue in vesicular GABA transport.

To determine biochemically whether the rat unc-47 homologue encodes the vesicular GABA transporter, the cDNA for RUNC-47 (SEQ ID NO: 3) was transfected and expressed in rat pheochromocytoma PC12 cells, using standard methods known in the art. PC12 cells contain synaptic-like microvesicles and support the activities of the vesicular monoamine transporters 18 as well as ACh transporter 19 but do not express detectable amounts of unc-47 homologue. Stable PC12 transformants expressing high levels of the putative transport protein were isolated by screening cell clones with fluorescent-tagged antibodies generated against the rat unc-47 homologue RUNC-47. Immunofluorescence reveals a punctate pattern consistent with localization to intracellular membrane vesicles (data not shown). A population of light vesicles was then isolated from two stable transformants and purified by differential centrifugation (Example 7).

Figure 11:
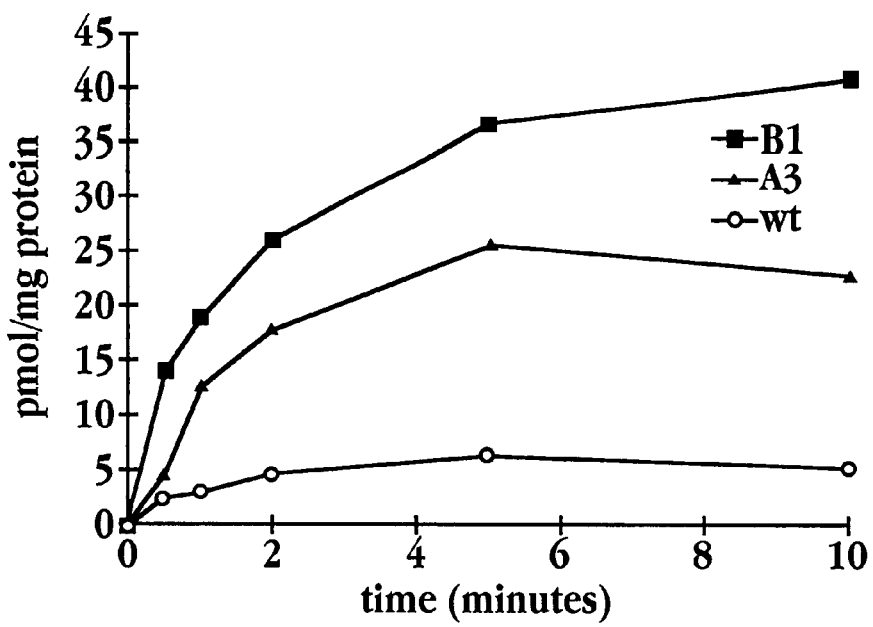
FIGS. 11 shows a plot of uptake of $^3$H-GABA by PC12 cell clones (A3, closed triangles; B1, closed squares) stably expressing the rat unc-47 homologue compared to uptake by untransfected PC12 cells (wt, open circles)
Figure 12:
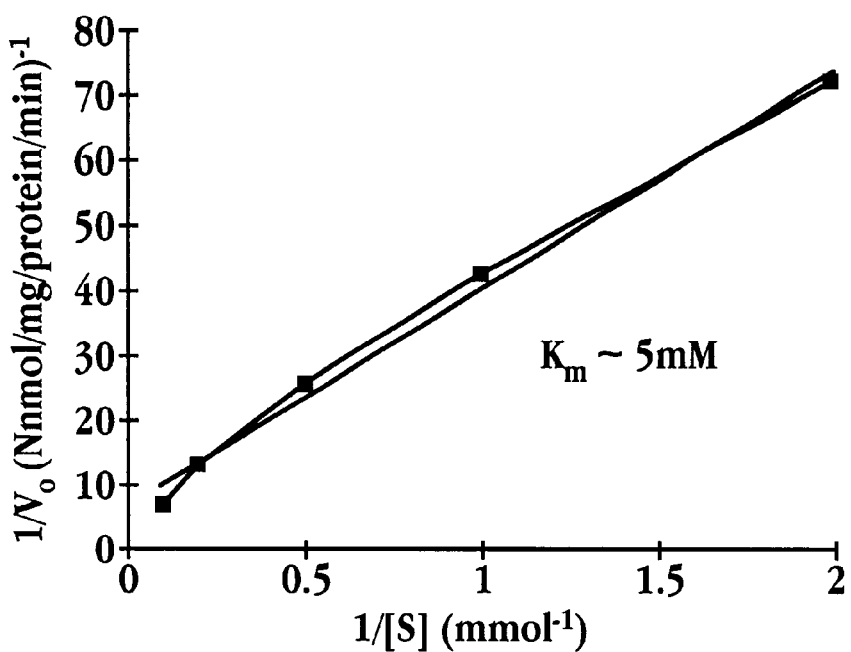
FIGS. 12 shows a Lineweaver-Burke plot of initial, maximal transport rate (Vo) in the presence of different concentrations of GABA (S, FM), with the linear approximation performed by standard regression analysis.

The PC-12-derived vesicles were tested for transport of GABA, according to the method described in Example 8. Results are shown in FIG. 11, which shows a plot of GABA accumulation vs. time in vesicles from the transfected cells (B1, A3) and control, non-transfected cells (wt). As shown, $^3$H-GABA accumulation was significantly higher in vesicles derived from transfected cells than the background uptake observed in membranes from untransfected cells. In addition, the transport activity present in transfected PC12 cells saturates with increasing concentrations of GABA and has a $K_m$ of approximately 5 mM, as determined by Lineweaver-Burke analysis (FIG. 12), consistent with previous observations using rat brain synaptic vesicles (Fykse and Fonnum, 1988; Hell, et al., 1988; Kish, et al., 1989; Burger, et al, 1991). Thus, from these studies, and according to an important feature of the present invention, it was concluded that the rat unc-47 homologue protein RUNC-47 functions as a vesicular GABA transporter (VGAT). Hereafter, the terms RUNC-47 and rVGAT are used interchangeably.

6. Characterization and Modulation of Vesicular Amino Acid Transport by Test Compounds Since there are no known potent and specific inhibitors of vesicular GABA transport, the functional properties of RUNC-47 were assessed to determine its relationship to the vesicular transport activity previously described in native brain synaptic vesicles.

Compounds structurally related to GABA that have been tested as inhibitors of GABA transport into synaptic vesicles were initially tested to assess ligand recognition and specificity. These studies were carried out in the transport assay detailed in Example 8, using synaptic vesicles prepared from transfected PC-12 cells, as described above and detailed in Example 7.

Figure 13:
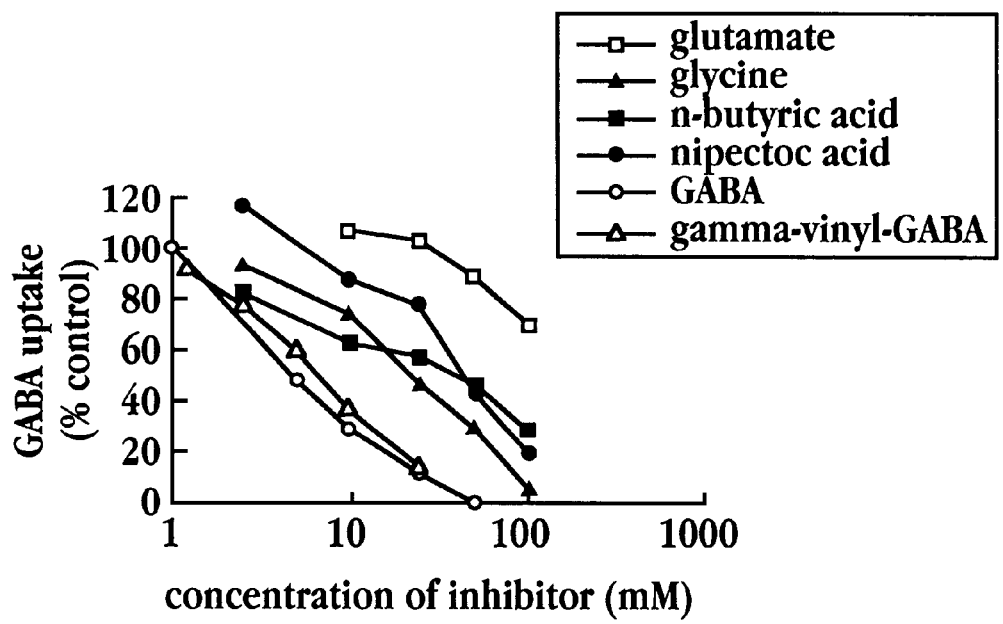
FIG. 13 shows a plot of GABA transport activity in the presence of competing amounts of unlabeled GABA and other test compounds.

To assess inhibitor activity, the vesicle preparation was incubated with varying concentrations of inhibitor in the presence of about 40 μM GABA (including radiolabeled GABA). Results are shown in FIG. 13 and Table 1. Similar to GABA transport into synaptic vesicles, the plasma membrane GABA transport inhibitor nipecotic acid inhibits rVGAT activity only weakly, and the excitatory amino acid transmitter glutamate does not inhibit rVGAT activity even at extremely high concentrations (Table 1). Thus, the analysis of ligand specificity also distinguishes rVGAT from these other neurotransmitter transporters. The GABA analogue n-butyric acid inhibits both rVGAT activity and GABA transport into brain synaptic vesicles, further supporting the identity of rVGAT as a vesicular GABA transporter. Previous studies using synaptic vesicles have also suggested inhibition of vesicular GABA transport by λ-vinyl-GABA (vigabatrin), an inhibitor of GABA transaminase and a potent anticonvulsant (Christensen, et al., 1991). This synthetic GABA analogue also inhibits the transport of $^3$H-GABA by rVGAT as potently as unlabelled GABA, supporting an additional site of action for this drug.

TABLE 1

Inhibition of GABA Transport by Structurally Related Compounds

| Inhibitor | IC$_{50}$ (mM) | SE |
|---|---|---|
| GABA | 4.75 | 0.3 |
| gamma-vinyl-GABA | 7.5 | 0.7 |
| glycine | 27.5 | 10.6 |
| n-butyric acid | 43.5 | 2.1 |
| nipecotic acid | 46 | 1.4 |
| glutamate | >100 | |

Previous studies of native brain synaptic vesicles have suggested that a single vesicular GABA transport activity also recognizes the inhibitory amino acid transmitter glycine as a substrate (Burger, et al., 1991). However, other studies have suggested a distinct transporter for glycine (Kish, et al:, 1989). Glycine inhibits GABA transport encoded by the rVGAT cDNA with relatively low potency. In addition, in studies carried out in support of the present invention, there was no significant uptake of $^3$H-glycine by the RUNC-47 PC-12 vesicle preparations, supporting the existence of a distinct vesicular transporter for glycine. However, according to the present invention, it is anticipated that a glycine synaptic vesicular transporter molecule is one or more of the synaptic vesicle amino acid transporter family members described by the present invention.

7. Bioenergetics of Synaptic Vesicle Transport

Functional analysis of rVGAT indicates that the synaptic vesicle amino acid transporters exhibit different bioenergetics, when compared to vesicular transporters for monoamines and ACh. Monoamine and ACh transport rely primarily on the chemical component (ΔpH) of the proton electrochemical gradient (ΔF$_{H+}$) (Schuldiner, et al., 1995; Liu, et al., 1997). Studies using native synaptic vesicles prepared from brain have indicated that vesicular GABA transport relies on the electrical component ΔΨ as well as ΔpH (Hell, et al., 1988; Kish, et al., 1989; Burger, et al, 1991).

Figure 14:
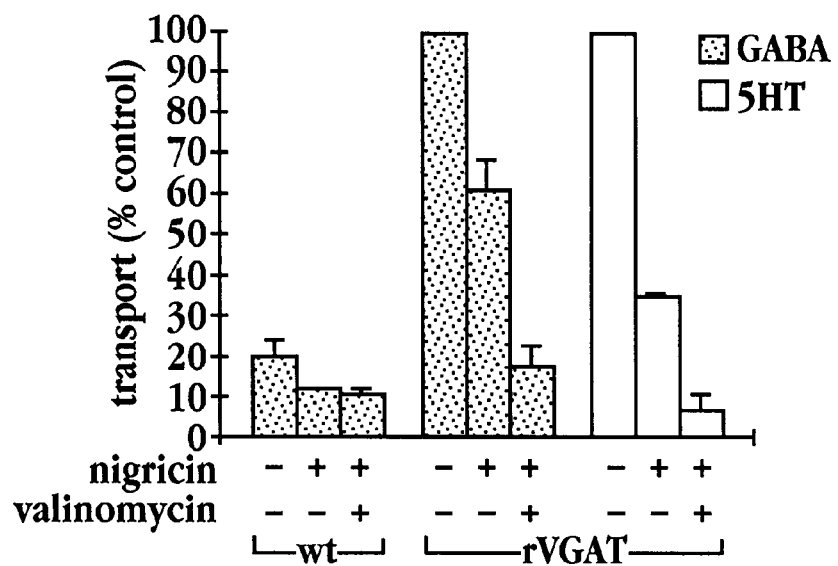
FIG. 14 shows a bar graph comparing vesicular GABA transport and vesicular monoamine transport in the absence or presence of one or both of metabolic inhibitors nigericin and valinomycin, where membranes prepared from PC12 cell clone B1 stably expressing rVGAT (middle) show considerably more GABA transport activity (filled bars) than membranes from untransfected cells (wt, left), where results are normalized to GABA transport (left and middle groups) and serotonin transport (right group) by rVGAT-expressing cells and the error bars represent the standard error of the mean.

In studies carried out in support of the present invention, the bioenergetics of rVGAT function was assessed using the ionophore nigericin, which exchanges K$^+$ for H$^+$, selectively dissipating ΔpH. Briefly, vesicles were prepared from PC12 cell clone B1 stably expressing rVGAT and from un-transfected cells. As shown in FIG. 14, membranes from the rVGAT expressing cells (rVGAT) show considerably more GABA transport activity (center group of shaded bars) than membranes from untransfected cells (wt, shaded group of bars to left of Figure). Nigericin (5 FM) inhibits GABA transport in the rVGAT transfected cells by approximately 40% and the addition of valinomycin (20 FM) to nigericin eliminates rVGAT activity, indicating greater dependence on ΔΨ than ΔpH.

Thus, these studies indicate that there is an additional role for ΔΨ in synaptic vesicle amino acid transport. Further, addition of both nigericin and valinomycin, an ionophore that mediates K$^+$ flux and so dissipates ΔΨ as well as ΔpH, eliminated rVGAT activity in transfected cells.

To compare directly the bioenergetics of vesicular GABA and monoamine transport, transport of serotonin by the same PC12 cell membrane preparations that contain rVGAT was examined. Previous work has demonstrated the expression of endogenous vesicular monoamine transporter 1 (VMAT1) on synaptic-like microvesicles in these cells (Liu, et al., 1994). As shown in FIG. 14, transport of serotonin by endogenous VMAT1 (right group of open bars) expressed in the same membranes from transfected PC12 cells that express VGAT shows approximately 65% inhibition by nigericin, indicating that VMAT1 depends to a greater extent on $\Delta pH$ than rVGAT. Since nigericin inhibits VMAT1 activity on these vesicles to a greater extent (approximately 65%) than it inhibits rVGAT activity, vesicular transport of serotonin has a greater dependence on $\Delta pH$. The addition of valinomycin to nigericin eliminates the residual VMAT1 activity, indicating a small role for $\Delta\Psi$. Thus, rVGAT and VMAT1 depend on both components of the electrochemical gradient but VMAT1 depends to a greater extent on $\Delta pH$, consistent with previous results using mixed populations of synaptic vesicles.

The analysis of GABA and monoamine transport activities expressed in the same population of membrane vesicles shows that rVGAT depends on $\Delta\Psi$ to a greater extent than VMAT1. Indeed, this difference in bioenergetic mechanism may account for the structural differences between these two classes of vesicular transporters.

8. Identification and Isolation of Synaptic Vesicle Amino Acid Transporter Family Members Identification of the unc-47 homologue as a vesicular GABA transporter provides the first insight into the molecular mechanism for vesicular transport of an amino acid neurotransmitter. The genetic analysis in *C. elegans* indicates that unc-47 is essential for GABA transmission. In addition, UNC-47 and its rat homologue both occur in GABAergic neurons, and their polytopic nature supports a role in vesicular transport. Biochemical characterization of the rat unc-47 homologue demonstrates GABA transport function with the affinity and ligand specificity reported for GABA transport by native synaptic vesicles. Since rVGAT failed to transport the other major inhibitory transmitter, glycine, into vesicles, it is likely that there is a distinct vesicular glycine transporter, which is likely a family member, as described herein. In addition, the novel class of proteins identified by UNC-47 and RUNC-47 (SEQ ID NO:1 and SEQ ID NO:2, respectively), further includes the rVT2 and rVT3 amino acid sequences presented herein as SEQ ID NO:26 and SEQ ID NO:28 and the nucleic acid sequences which encode them presented herein as SEQ ID NO:25 and SEQ ID NO:27, respectively. This novel class of proteins is anticipated to include the transporters for excitatory amino acid transmitters such as glutamate which also depend on $\Delta\Psi$.

Thus further family members can be identified and characterized in accordance with the guidance provided herein. That is, using a molecular biological approach, appropriate cDNA probes can be generated from the sequences disclosed herein, and used to probe cDNA libraries formed from regions of human brain known to be enriched in cells from a selected amino acid neurotransmitter, according to principles and methods well known in the art.

Generally, the present invention describes a novel family of synaptic vesicle amino acid transporter proteins, based on sequence identities between invertebrate and vertebrate species. In one aspect, the family can be defined by the discovered synaptic vesicle amino acid transporter protein from *C. elegans*, and as having an amino acid sequence which has substantial sequence identity to portions of the *C. elegans* unc-47 expression product UNC-47. Moreover, the invention includes sequences which are variants of the basic synaptic vesicle amino acid transporter protein sequence, as defined herein. Such variants can include substitution of amino acids from a common substitution class, to provide a conservative or neutral variant. Standard substitution classes are the six classes based on common side chain properties and highest frequency of substitution in homologous proteins in nature, as determined, for example, by a standard Dayhoff frequency exchange matrix (Dayhoff). These classes are Class I: Cys; Class II: Ser, Thr, Pro, 4Hyp, Ala, and Gly, representing small aliphatic side chains and OH-group side chains; Class III: Asn, Asp, Glu, and Gln, representing neutral and negatively charged side chains capable of forming hydrogen bonds; Class IV: His, Arg, and Lys, representing basic polar side chains; Class V: Ile, Val, and Leu, representing branched aliphatic side chains, and Met; and Class VI: Phe, Tyr, and Trp, representing aromatic side chains. In addition, each group may include related amino acid analogs, such as ornithine, homoargirine, N-methyl lysine, dimethyl lysine, or trimethyl-lysine in class IV, and cyclohexylalanine or a halogenated tyrosine in Group VI. Further, the classes may include both L and D stereoisomers, although L-amino acids are preferred for substitutions.

Another subset of the amino acid synaptic vesicle transporter protein family of the invention includes vertebrate or mammalian forms of such transporter proteins. According to a general formula, such proteins contain at least 10 putative transmembrane domain regions, as depicted in FIGS. 1A and B.

Additional family members may also be identified using the genetic approach outlined with reference to *C. elegans* unc-47, above. That is, the present invention reveals that UNC-47 and RUNC-47 show varying degrees of identity to peptide sequences derived from *C. elegans, S. cerevisiae* and plants. Several of the plant sequences mediate amino acid transport and use a proton electrochemical gradient as the driving force (Fischer, et al., 1995), suggesting functional as well as structural identity to UNC-47 and rVGAT. Since these plant permeases catalyze cotransport of amino acids and protons rather than the proton exchange mediated by rVGAT, it is likely that the sequence identity reflects general features of substrate recognition and proton movement rather than the precise mechanism of bioenergetic coupling. However, probes derived from such amino acid transport proteins may reveal mammalian homologs for particular synaptic vesicle amino acid transporters, according to the principles detailed above.

III. Polynucleotides, Vectors and Cells for Expression of Synaptic Vesicle Amino Acid Transporter Proteins In accordance with additional features, the present invention includes polynucleotides which encode the amino acid synaptic vesicle transporter protein family members, as well as expression vectors and transformed cells capable of expressing such proteins. These compositions are useful, for example, in producing protein compositions for use in the various screening and diagnostic assays discussed below.

Primary coding sequences can be identified and isolated using probes based on the sequence information provided herein. Particularly, nucleotide probes derived from the transmembrane regions (corresponding to peptides from RUNC-47 identified as SEQ ID NOs: 5–14, or to peptides from UNC-47 identified as SEQ ID NOs: 15–24, shown in FIGS. 1A and B) can be used to isolate DNA that encodes for additional family members. Methods for synthesis of polynucleotides in accordance with this aspect of the invention are known in the art.

According to another aspect, the invention includes DNA fragments of the nucleic acid sequence encoding SEQ ID NO: 1 and SEQ ID NO: 2. Also forming part of the present invention are nucleotide sequences that contain alternate codons effective to encode transporter protein family members in accordance with the present invention. Such alternate codons may be selected based on codon preferences characteristic of a particular cell type in which the encoded proteins are to be expressed, or may be selected based on known codon equivalencies, according to methods well known in the art. Particular sequences include the isolated cDNA which encodes UNC-47 (SEQ ID NO: 3), as well as the isolated cDNA which encodes RUNC-47 (SEQ ID NO: 4). These sequences have been deposited in GenBank as AF031935 and AF030253, respectively.

More generally, it is within the purvue of the present invention to design polynucleotides based on the polypeptides described above. That is, taking for example, the 10 putative transmembrane domain regions which are highly conserved among members of the transporter family exemplified by RUNC-47, a nucleotide can be designed and constructed that encodes regions substantially similar to each of the regions shown in FIGS. 1A and B as SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, and SEQ ID NO: 14. Other, more specific constructs described herein can also be designed and constructed using methods well known in the art. According to one aspect of the invention, the polynucleotide molecule for encoding vertebrate forms of the transporter protein may include the highly conserved 3' untranslated region found to have approximately 95% sequence identity among rat, mouse and human forms of the gene. This region provides for more efficient recombinant expression of the protein.

The present invention also includes expression vectors suitable for use in a method of recombinantly producing synaptic vesicle amino acid transporter molecules, such as are described above. The vector includes a polynucleotide containing an open reading frame that encodes the transporter polypeptide described above, and operably linked to regulatory sequences effective to express the open reading frame in a selected host cell. The regulatory sequences may include sequences useful for targeting or secretion of the polypeptide. Such sequences may be endogenous (such as the normally occurring GhR leader sequences) or heterologous (such as a secretory signal recognized in yeast, mammalian cells, insect cells, tissue culture or bacterial expression systems). In the expression vector, regulatory sequences may also include, 5' to the nucleic acid sequence, a promoter region and an ATG start codon in-frame with the polypeptide coding sequence, and 3' to said coding sequence, a translation termination signal followed by a transcription termination signal.

In accordance with the present invention, synaptic vesicle amino acid transporter proteins may be produced recombinantly by any of a number of methods available for expression of proteins. Expression can be carried out in any of a number of cellular expression systems. Possible host cells include but are not restricted to bacterial, yeast, insect, and mammalian cells.

Proteins can be expressed intracellularly or extracellularly. For bacterial expression, the proteins can be expressed as inclusion bodies or in soluble form. It is appreciated that expression in a particular system may be optimized by tailoring codons to the particular cell type in which expression is to occur. Hence polynucleotides encompassed by the present invention shall include polynucleotides encoding for the protein of interest, as modified for optimal expression in any given expression system, so long as the resulting expression product has overall identity that is within the range identified herein. Such designing can be effected with the aid of codon usage or preference tables such as are known in the art.

IV. Antibodies

In accordance with another aspect, the invention includes polyclonal or monoclonal antibodies specific against synaptic vesicle amino acid transporter proteins, as described herein. Such antibodies may be prepared by conventional techniques known in the art. The immunogen used is an isolated or purified protein or protein fragment, preferably conjugated to a carrier protein. A suitable animal, such as rabbit or mouse, is injected according to immunological protocols generally known in the art, e.g., Harlow, E., et al., 1988, pp. 93–115. Typically, the animal is injected subcutaneously with the immunogen in an adjuvant, and booster immunizations are given by subcutaneous or intramuscular injection every 2–3 weeks. Blood is collected at intervals, e.g. 1–2 weeks after each immunization injection. Antisera may be titrated to determine antibody formation with respect to p68-PK, according to standard immunoprecipitation methods (Harlow, E., et al., 1988, pp. 423470).

To prepare a monoclonal antibody MAb specific against a specific transporter protein as described herein, the immunogen described above is used to immunize an animal, such as a mouse, from which antigen-specific lymphocytes can be obtained for immortalization. These methods are used to generate a hybridoma cell line which has a high specificity toward the protein of interest. Briefly, in producing the cell line, mice are immunized by intraperitoneal injection of a transporter protein immunogen. Several, e.g., 8 weeks after initial immunization, spleen cells are harvested, and fused with a standard myeloma cell line. Selection for successful fusion products is in HAT medium, according to published methods (see, generally, Harlow, E., et al., 1988, pp. 196–212). Successful fusion products are then screened for immunoreactivity with the antigen, for example by antigen capture in solution by immunoprecipitation or by ELISA methods known in the art. Cell lines which show high affinity binding to the protein antigen may be subcloned by limiting dilution and further screened for production of antibodies with high binding affinity for the protein antigen by methods known in the art.

To produce the antibody reagent, the hybridoma cell line is grown in a suitable medium, such Dulbecco's modified Eagle's (DME) or RPMI 1640 media (Harlow, E., et al., 1988, pp. 247–270). MAbs are harvested from the medium and can be concentrated and stored according to published methods (Harlow, E., et al., 1988, pp. 271–318).

V. Utility

This section provides exemplary utilities of the compositions of the present invention. It is by no means intended to limit the use of the invention.

Members of the family of synaptic vesicle amino acid transporter proteins described herein can be used, for example, in a method of identifying candidate compounds that are capable of modulating amino acid transport into synaptic vesicles. It is understood, as described in more detail below, that such compounds may provide useful therapeutics for treating various disorders of the central and/or peripheral nervous system. According to this aspect of the invention, compounds are selected for their abilities to either enhance or inhibit amino acid transport into synaptic vesicles.

While their are a number of formats for such an assay system, general steps will usually include (a) contacting a test compound with a selected transporter protein under conditions in which the activity of the transporter protein can be measured, and (b) measuring the effect of the test compound on the transport activity of the transporter protein. The compound is selected as a candidate compound if its effect on the activity of the transporter protein is above a selected threshold level.

In practice, selection of transport modulating compounds may be best measured in a synaptic vesicle preparation such as that described in Example 7 herein. Such a preparation can be made from a number of sources. One particularly useful source is the PC-12 cells described herein, which lack or have very low levels of endogenous amino acid transport activity associated with synaptic vesicles. Here, the cells are first transfected with a vector containing a coding sequence for the transporter protein of interest, and vesicular transport is measured according to methods known in the art. A representative assay format is provided in Example 8. Variations of this assay will be recognized by persons having skill in the art.

Enhancement or inhibition of uptake can be measured according to the methods contemplated by the present invention.

According to a further aspect, the invention includes a method of treating a subject having a neuropsychiatric condition characterized by neuronal deficiency of GABA. Here, the subject is given a pharmaceutically effective amount of a compound found to be capable of enhancing amino acid transport into synaptic vesicles by modulating the activity of one or more of the family of synaptic vesicle transport proteins described herein, e.g., a GABA transporter, such as the protein having the sequence SEQ ID NO: 2, or a protein having substantial sequence identity thereto, and also having GABA transport activity. Compounds are identified as having GABA-modulating activity defined as GABA-inhibitory or GABA-enhancing activity in an assay such as the assay described above. Once identified, such compounds are tested for toxicity and then for in vivo efficacy in appropriate animal models. Pharmaceutically effective carriers and doses can be extrapolated for humans using methods well known in the art. Particularly useful compounds in this context are those which enhance GABA uptake, and which may produce sedative or anxiolytic effects, in accordance with the present invention.

The following examples illustrate, but in no way are intended to limit the present invention.

MATERIALS AND METHODS

EXAMPLE 1

Cloning of unc-47

A pool containing 10 ng/μl each of cosmid E03F9, ZK1128, F55E6, T20G5, and K08E5 (Jorgenson, E. M., Dept. of Biology, University of Utah, Salt Lake City, Utah) was injected along with 80 ng/μl of EK L15 (lin-15+) marker plasmid (Clark, et al., 1994). The DNA was injected into the syncytial gonads of unc-47(e307); lin-15 (n765ts) mutant worms (Caenorhabditis elegans). Five lin-15+ lines were established and all animals were rescued for the unc-47 mutant phenotypes. A 5.2 kb BamHI fragment subcloned from T20G5 rescued unc-47(e307) mutants. The 5.2 kb BamHII fragment was used to screen 350,000 plaques from an oligo dT-primed λ ZAP cDNA library made from mixed stage RNA, and a single positive (B1) was identified. To isolate additional cDNAs, 400,000 plaques of a second oligo dT-primed mixed stage cDNA library were screened and four positives were isolated (O K1-4). Sequence analysis showed that the B1 cDNA uses an alternative splice donor site in exon five, resulting in deletion of the eighth and part of the ninth transmembrane domains (TMDs). However, PCR amplification of reverse-transcribed cDNA demonstrated that this mRNA transcript is extremely rare and presumably results from aberrant splicing. The 5' end of unc-47 was identified by PCR amplification of first strand cDNA prepared from mixed stage poly-A$^+$ RNA. Sequence analysis of the product revealed an SL1 splice leader immediately 5' to the ATG start codon.

The reference allele, e307 (Brenner, S., Genetics 77, 71–94, 1974) is a G to A transition of the absolutely conserved G in the splice acceptor site between exons five and six (FIG. 1). A second strong mutation, n2476, is a 238 base pair deletion which removes parts of exons three and four; this deletion causes a frameshift at residue 175 and the open reading frame terminates after another 115 amino acids indicating that this allele is a molecular null. Finally, n2409 is a G to A transition which changes a glycine to arginine at residue 462 in a predicted transmembrane segment. To prepare genomic DNA from mutant alleles e307, n2476, and n2409, approximately 20 homozygous mutant worms were washed three times with M9 salts to remove bacteria, resuspended in 5 μl water and boiled for 5 minutes. Four μl 10 mM Tris/1 mM EDTA (TE) buffer and 1 μl of 1 mg/ml proteinase K were added and the mixture incubated at 45° C. for 1 hour. Proteinase K was inactivated by boiling for 30 minutes and 1 μl of this DNA preparation Was used for PCR amplification. Amplified fragments were purified and sequenced using the Cyclist TM Taq DNA sequencing kit (Stratagene).

EXAMPLE 2

GFP Expression Constructs

To construct the U47GFPNTX transcriptional fusion, Green Fluorescent Protein (GFP) and unc-54 RNA termination sequences were amplified from pPD95.85 according to methods well known in the art, using primers that engineered an in-frame BspHI site onto the 5' end of GFP. Using an internal BspHI site which includes 553 bp of the unc-54 terminator, the amplified fragment was cloned into the BspHI site in the unc-47-rescuing 5.2 kb BamHI fragment. 30 ng/μl U47GFPNTX together with 35 ng/μl EK L15 (lin-15+) DNA were injected into the gonads of lin-15 (n765ts) mutants (McIntire). Three lines carrying an extrachromosomal array of both U47GFPNTX and EK L15 were established and all three lines expressed GFP in the GABAergic neurons. The extrachromosomal array from one line was integrated into chromosome X by X-ray integration to generate the strain EG1285: lin-15(n765ts); oxIn12.

To construct the U47GFPCTL translational fusion, A SalI site was engineered into the carboxy terminus of the unc-47 protein coding sequence, two residues N-terminal to the UAA stop codon. GFP was amplified by PCR with primers that engineered an in-frame SalI site on each end of the GFP fragment and then cloned into the SalI site created at the carboxyl terminus of UNC-47. 30 ng/μl U47GFPCTL and 35 ng/μl EK L15 (lin-15$^+$) DNA were injected into the gonads of lin-15(n765ts) and into lin-15(n765ts);unc-47 (e307) mutant worms and three lin-15(n765ts) lines were established that contained an extrachromosomal array of both U47GFPCTL and lin-15$^+$. Four lin-15(n765ts); unc-47 (e307) lines were obtained that contained both U47GFPCTL and lin-15$^+$ in an extrachromosomal array. Worms in two lines had strong GFP expression at the nerve terminals and almost all lin-15+ animals were also unc-47$^+$.

To express. U47GFPCTL in the unc-104(e1265) mutant background, the oxEx68 [U47GFPCTL; lin-15+] extrachromosomal array was crossed into unc-104(e1265); lin-15 (n765ts) mutants to generate EG1300: unc-104; lin-15; oxEx68 (McIntire, et al., 1993).

EXAMPLE 3

PCR Amplification and Library Screening

A search of the available expressed sequence tag (EST) database with the predicted amino acid sequence of UNC-47 identified mouse EST 252177 as a possible vertebrate homologue. Using oligonucleotide primers based on 252177, a fragment was amplified by the polymerase chain reaction (PCR) from a pooled mouse brain cDNA library. Briefly, 200 ng template DNA was amplified in a 50 $\mu$l reaction containing 25 mM Tris, pH 8.3, 50 mM KCl, 3 mM $MgCl_2$, 100 pmol each oligonucleotide, 100 $\mu$M dNTPs and 1 $\mu$l Taq polymerase for 30 cycles involving denaturation at 92° C. for 1 minute, annealing at 66° C. for 1 minute and extension at 72° C. for 1 minute. After gel purification, the fragment was radiolabelled by PCR amplification under similar conditions in the presence of 2 $\mu$M non-radioactive dCTP and 1 $\mu$M $^{32}$P-dCTP and used to screen a mouse brain bacteriophage cDNA library by aqueous hybridization at 47.5° C. (Liu, et al., 1992b). After washing at 52° C., positively hybridizing phage were identified by autoradiography, purified by two sequential rounds of screening, and the cDNA inserts rescued. After confirmation of the close sequence identity to unc-47, this fragment was radiolabelled by random priming and used to screen a rat brain bacteriophage cDNA library as described above. After characterization of the resulting cDNA clones, the 5' end of the cDNA was amplified by PCR from a different rat brain cDNA library using oligonucleotide primers from the known rat sequence together with a primer flanking the vector insertion site. Another oligonucleotide primer based on the additional sequence was then used to amplify the 5' end of the cDNA from the library with Pfu polymerase rather than Taq to minimize mutations. This 5' fragment was then joined to a cDNA clone isolated by hybridization at a common BglII restriction site. The dideoxy chain termination method was used to confirm the sequence of the cDNA on both strands.

EXAMPLE 4

Northern Analysis

Five $\mu$g poly $A^+$ RNA prepared from different rat tissues was separated by electrophoresis through formaldehyde-agarose and transferred to nylon membranes. Staining with ethidium bromide revealed approximately equal amounts of RNA in each lane. After hybridization in 50% formamide (Liu, et al., 1992b) to the unc-47 homologue cDNA radio-labelled by random priming, the filters were submitted to autoradiography with an enhancing screen.

EXAMPLE 5

In Situ Hybridization

Adult rats were anesthetized with pentobarbital and perfused with 4% paraformaldehyde in phosphate-buffered saline (PBS). After dissection, the brains were post-fixed in the same solution, cryoprotected in 30% sucrose/PBS and 15 $\mu$m sections hybridized at 52° C. in 50% formamide containing 0.3 M NaCl, 20 mM Tris, pH 7.4, 5 mM EDTA, 10 mM $NaH_2PO_4$, 1×Denhardt's solution, 10% dextran sulfate and 0.5 mg/ml yeast RNA to $^{35}$S-labelled RNA probes transcribed from linearized plasmid templates and hydrolyzed in alkali to approximately 300 nucleotide fragments (Sassoon, D. & Rosenthal, N. in *Guide to Techniques in Mouse Developmeny* (eds. Wassarman, P. M. & DePamphilis, M. L.), 384404, Academic Press, Inc., San Diego, 1993). After washes in 50% formamide and digestion with RNase A, the slides were subjected to autoradiography.

EXAMPLE 6

Immunofluorescence

Primary hippocampal cultures were grown on poly-D-lysine-coated glass coverslips for two weeks, fixed in 4% paraformaldehyde/PBS for 20 minutes, rinsed in PBS, blocked in 0.02% saponin, 2% BSA (Bovine Serum Albumin), 1% fish skin gelatin/PBS (blocking buffer) for one hour and incubated for 90 minutes with anti-rVGAT polyclonal rabbit prepared using a GST-C terminal RUNC-47 fusion protein conjugated to keyhole limpet hemocyanin (KLH) as immunogen, and anti-synaptophysin monoclonal mouse antibodies diluted 1:100 in blocking buffer, all at room temperature. The cells were then washed, incubated in secondary anti-rabbit antibody conjugated to fluorescein and anti-mouse antibody conjugated to rhodamine (both from Cappel), both diluted 1:100, washed, the coverslips mounted on glass slides and viewed under epifluorescence.

EXAMPLE 7

Membrane Preparation

The rat unc-47 homologue cDNA subcloned into the plasmid expression vector pcDNA3-Amp (InVitrogen; Carlsbad, Calif.) was introduced into PC12 cells by electroporation (Grote, et al., *Cell* 81, 581–589, 1995). The cells were then selected in 800 $\mu$g/ml G418 (effective) and the resulting clones examined by immunofluorescence (Liu, et al., 1994) using a rabbit polyclonal antibody. Using the two cell clones with the highest level of immunoreactivity, membranes were prepared by first resuspending the washed cells in 0.3 M sucrose, 10 mM Hepes-KOH, pH 7.4 SH buffer) containing 0.2 mM diisopropylfluorophosphate (DFP), 1 $\mu$g/ml pepstatin, 2 $\mu$g/ml aprotinin, 2 $\mu$g/ml leupeptin, 1 $\mu$g/ml E64 and 1.25 mM MgEGTA. The cells were then disrupted by homogenization at 4° C. through a ball-bearing device at a clearance of 10 $\mu$m. The nuclear debris was sedimented at 100 g for 5 minutes and heavier membranes were eliminated by centrifugation at 27,000 g for 1 hour The remaining light membrane vesicles were sedimented at 65,000 g for 1 hour and resuspended in SH containing the same protease inhibitors at a final concentration of approximately 10 $\mu$g protein/$\mu$l.

EXAMPLE 8

Transport Assay

To initiate the reaction, 10 $\mu$l membranes was added to 200 $\mu$l SH buffer containing 4 mM $MgCl_2$, 4 mM KCl, 4 mM ATP, 40 $\mu$M unlabelled GABA and 2 $\mu$Ci $^3$H-GABA (NEN). Incubation was performed at 29° C. for varying intervals and the reaction was terminated by rapid filtration (Supor 200, Gelman; AnnArbor, Mich.), followed by immediate washing with 6 ml cold 0.15 M KCl. Background uptake was determined by incubation at 4° C. for 0 minutes. The bound radioactivity was measured by scintillation counting in 2.5 ml Cytoscint (ICN). To determine $K_m$, unlabelled GABA was added at a range of concentrations and uptake was measured at 30 seconds. Nigericin and valinomycin were dissolved in ethanol and added to final concentrations of 5 µM and 20 µM respectively. Transport measurements were performed in duplicate and repeated three or more times using at least two different membrane preparations.

While the invention has been described with reference to specific methods and embodiments, it will be appreciated that various modifications and changes may be made without departing from the invention. All patent and literature references cited herein are hereby incorporated by reference in their entireties.

It is claimed:

1. An isolated DNA fragment that encodes an amino acid synaptic vesicle transporter protein that is capable of effecting the passage of GABA into a synaptic vesicle, and which is capable of hybridizing to the complement of the nucleic acid disclosed in SEQ ID NO: 3 under high stringency conditions as follows: hybridization at 65° C. in about 5×SSPE and washing at 65° C. in about 0.1×SSPE.

2. The DNA fragment of claim 1, wherein the amino acid synaptic vesicle transporter protein has a sequence that is at least 90% identical to SEQ ID NO: 1.

3. The DNA fragment of claim 2, having the sequence SEQ ID NO: 3.

4. An isolated DNA fragment that encodes an amino acid synaptic vesicle transporter protein which contains at least 10 putative transmembrane domain regions, each of which has a sequence that is at least 90% identical to a transmembrane region having a sequence which is disclosed in SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14, respectively, and wherein said protein is capable of effecting the passage of GABA into a synaptic vesicle.

5. The DNA fragment of claim 4, wherein the transporter protein a sequence that is at least 90% identical to SEQ ID NO: 2.

6. The DNA fragment of claim 4 wherein said DNA fragment further includes a 3' untranslated region having at least 90 to 95% sequence identity to the 3' untranslated region present in SEQ ID NO:4.

7. The DNA fragment of claim 6, having the sequence SEQ ID NO: 4.

8. A recombinant expression vector, comprising a DNA fragment coding for an amino acid synaptic vesicle transporter protein containing an amino acid sequence which has at least 90% sequence identity to SEQ ID NO: 2, and wherein said protein is capable of effecting the passage of GABA into a synaptic vesicle, and operably linked to said fragment, a regulatory sequence capable of promoting expression of the protein in a selected host.

9. The vector of claim 8, wherein the fragment encodes at least 10 putative transmembrane domain regions wherein the 10 putative transmembrane domain regions are sequences at least 90% identical to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14, respectively.

10. The vector of claim 8, which further includes a 3' untranslated region having at least 90 to 95% sequence identity to the 3' untranslated region present in SEQ ID NO: 4.

11. A recombinant cell transfected with the vector of claim 8 or claim 10, and having the protein expressed by said vector.

12. The cell of claim 11, wherein the amino acid synaptic vesicle transporter protein has a sequence which has at least 90% sequence identity to SEQ ID NO: 2.

13. The cell of claim 11, wherein the amino acid synaptic vesicle transporter protein includes at least 10 transmembrane domain regions wherein the 10 putative transmembrane domain regions are sequences at least 90% identical to SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14, respectively.

* * * * *